(12) United States Patent
Mertens-Talcott et al.

(10) Patent No.: US 11,523,998 B2
(45) Date of Patent: Dec. 13, 2022

(54) ANTI-INFLAMMATORY FORMULATIONS AND USES THEREOF INCLUDING A COMBINATION OF PALMITOYLETHANOLAMIDE AND PLANT-BASED POLYPHENOLS

(71) Applicants: The Texas A&M University System, College Station, TX (US); Core Vibe Health, Inc., Ojai, CA (US)

(72) Inventors: Susanne U. Mertens-Talcott, College Station, TX (US); Ariela Betsy Thomas, College Station, TX (US); Vinicius De Paula Venancio, College Station, TX (US); Geoffrey R. Pfeifer, Ojai, CA (US); Blake M. Ebersole, Carmel, IN (US)

(73) Assignees: The Texas A&M University System, College Station, TX (US); Core Vibe Health Inc., Ojai, CA (US)

( * ) Notice: Subject to any disclaimer, the term of this patent is extended or adjusted under 35 U.S.C. 154(b) by 0 days.

(21) Appl. No.: 16/442,075

(22) Filed: Jun. 14, 2019

(65) Prior Publication Data

US 2019/0380988 A1  Dec. 19, 2019

Related U.S. Application Data

(60) Provisional application No. 62/685,060, filed on Jun. 14, 2018.

(51) Int. Cl.
| | | |
|---|---|---|
| *A61K 31/20* | (2006.01) | |
| *A61P 29/00* | (2006.01) | |
| *A61K 9/00* | (2006.01) | |
| *A61K 31/12* | (2006.01) | |
| *A61K 31/366* | (2006.01) | |

(52) U.S. Cl.
CPC ............ *A61K 31/20* (2013.01); *A61K 9/0014* (2013.01); *A61K 31/12* (2013.01); *A61K 31/366* (2013.01); *A61P 29/00* (2018.01)

(58) Field of Classification Search
CPC combination set(s) only.
See application file for complete search history.

(56) References Cited

FOREIGN PATENT DOCUMENTS

| | | |
|---|---|---|
| EP | 2921167 | 9/2015 |
| EP | 3130336 | 2/2017 |
| EP | 3409275 | 12/2018 |
| EP | 3449943 | 3/2019 |
| WO | 2016183134 | 11/2016 |

OTHER PUBLICATIONS

Hewlings (Curcumin: A Review of Its' Effects on Human Health, Foods 2017, 6, 92; doi:10.3390, Oct. 2017, p. 1-11).*

Domenico Britti et al., A novel composite 1-3,5-27 formulation of palmitoylethanolamide and quercetin decreases inflammation and relieves pain in inflammatory and osteoarthritic pain models, BMC Veterinary Research, vol. 13, No. 1, Aug. 2, 2017, XP055544779, DOI: 10.1186/sl2917-017-1151-z.
International Search Report dated Sep. 20, 2019 for International Application No. PCT/US2019/037305.
Cerrato, et al. Effects of palmitoylethanolamide on immunologically induced histamine, PGD2 and TNFa release from canine skin mast cells. Vet. Immunol Immunopathol., 2010, 133:9-15.
Chou, et al. Quantitative analysis of dose-effect relationships: the combined effects of multiple drugs or enzyme inhibitors. Adv. Enzyme Regul., 1984, 22:27-55.
Chuang, et al. Quercetin is equally or more effective than resveratrol in attenuating tumor necrosis factor-a-mediated inflammation and insulin resistance in primary human adipocytes 1-3. Am. J. Clin. Nutr., 2010, 92:1511-1521.
Cordaro, et al. Neuroprotective Effects of Co-UltraPEALut on Secondary Inflammatory Process and Autophagy Involved in Traumatic Brain Injury. Neurotrauma, 2016, 33:132-46.
Cremon, et al. Randomised clinical trial: the analgesic properties of dietary supplementation with palmitoylethanolamide and polydatin in irritable bowel syndrome. Aliment. Pharmacol. Ther., 2017, 45: 909-922.
Di Paola, et al. Co-micronized palmitoylethanolamide/polydatin treatment causes endometriotic lesion regression in a rodent model of surgically induced endometriosis. Front. Pharmacol., 2016, 7:1-13.
Guha, et al. LPS induction of gene expression in human monocytes. Cellular signalling 13.2, 2001: 85-94.
Karuppagounder, et al. Molecular targets of quercetin with anti-inflammatory properties in atopic dermatitis. Drug Discov. Today, 2016, 21: 632-639.
Kocaadam, et al. Curcumin, an active component of turmeric (*Curcuma longa*), and its effects on health. Crit. Rev. Food Sci. Nutr., 2017, 57: 2889-2895.

(Continued)

*Primary Examiner* — Kathrien A Cruz
(74) *Attorney, Agent, or Firm* — Thomas | Horstemeyer, LLP

(57) ABSTRACT

Pharmaceutical or nutraceutical formulations are provided for treating inflammation in a subject in need thereof, as well as methods of treating inflammation in a subject in need thereof by administering one of the formulations. In some aspects, the pharmaceutical or nutraceutical formulation includes an effective amount of (i) palmitoylethanolamide or a derivative thereof, and (ii) one, two, three or more different small-molecule polyphenols or derivatives thereof to alleviate one or more causes or symptoms of the inflammation in the subject. In some aspects, the formulations include all three, e.g. the formulations includes (i) palmitoylethanolamide or a derivative thereof, (ii) quercetin or a derivative thereof, and (iii) curcumin or a derivative thereof. In some instances, the components (i)-(iii) discussed above are present at a mass ratio of about (i) 4 mg to 6 mg of palmitoylethanolamide or a derivative thereof to (ii) about 0.5 to 2.5 mg curcumin or a derivative thereof, and (iii) about 0.5 mg to 1.5 mg quercetin or a derivative thereof.

10 Claims, 22 Drawing Sheets

(56) References Cited

OTHER PUBLICATIONS

Murray, et al. Protective and pathogenic functions of macrophage subsets. Nat. Rev. Immunol., 2011, 11: 723-737.
Parralla, et al. PEA and luteolin synergistically reduce mast cell-mediated toxicity and elicit neuroprotection in cell-based models of brain ischemia. Brain Res., 2016, 1648-409-417.
Vaia, et al. Palmitoylethanolamide reduces inflammation and itch in a mouse model of contact allergic dermatitis. Eur. J. Pharmacol., 2016, 791: 669-674.
Caltagirone, et al. Co-ultramicronized Palmitoylethanolamide/Luteolin in the Treatment of Cerebral Ischemia: from Rodent to Man. Transl. Stroke Res., 2016, 7:54-69.
Crupi, et al. Co-Ultramicronized Palmitoylethanolamide/Luteolin Promotes Neuronal Regeneration after Spinal Cord Injury. Frontiers in Pharma., 2016, 7:1-12.
Indraccolo, et al. Effect of palmitoylethanolamide-polydatin combination on chronic pelvic pain associated with endometriosis: Preliminary observations. European Journal of Obstetrics & Gynecology and Reproductive Biology, 2010, 150: 76-79.
Impellizzeri, et al. Palmitoylethanolamide and luteolin ameliorate development of arthritis caused by injection of collagen type II in mice. Arthritis research & therapy, 2013, 15: 1-14.
Indraccolo, et al. Micronized palmitoylethanolamide/trans-polydatin treatment of endometriosis-related pain: a meta-analysis. Ann Ist Super Sanita, 2017, 53(2): 125-134.

Paterniti, et al. A new co-ultramicronized composite including palmitoylethanolamide and luteolin to prevent neuroinflammation in spinal cord injury. J. Neuroinflammation, 2013, 10:91.
Gugliandolo, et al. Palmitoylethanolamide and Polydatin combination reduces inflammation and oxidative stress in vascular injury. Pharma. Res., 2017, 123: 83-92.
Bertolino, et al. Beneficial Effects of Co-Ultramicronized Palmitoylethanolamide/Luteolin in a Mouse Model of Autism and in a Case Report of Autism. CNS Neuroscience & Therapeutics, 2017, 23: 87-98.
Cordaro, et al. Effects of a co-micronized composite containing palmitoylethanolamide and polydatin in an experimental model of benign prostatic hyperplasia. Toxicology and Applied Pharmacology, 2017, 329:231-240.
Esposito, et al. A new co-micronized composite containing palmitoylethanolamide and polydatin shows superior oral efficacy compared to their association in a rat paw model of carrageenan-induced inflammation. Eur. J. of Pharma. 2016, 782: 107-118.
Siracusa, et al. (2016). The Association of Palmitoylethanolamide with Luteolin Decreases Autophagy in Spinal Cord Injury. Molecular Neurobiology, 53(6), 3783-3792.
Karuppagounder, et al. Resveratrol attenuates HMGB1 signaling and inflammation in house dust mite-induced atopic dermatitis in mice. Int. Immunopharmacol., 2014, 23: 617-623.

* cited by examiner

*significantly different from Control ($p < 0.05$; ANOVA-Dunnet's Test)

*significantly different from Control ($p < 0.05$; ANOVA-Dunnet's Test)

significantly different from each other (p < 0.05; ANOVA-Sidak's Test).

significantly different from each other (p < 0.05; ANOVA-Sidak's Test).

* significantly different from LPS at $p < 0.05$; ANOVA-Dunnet's Test)

* significantly different from LPS at $p < 0.05$; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at p < 0.05; ANOVA-Dunnet's Test)

* significantly different from LPS at $p < 0.05$; ANOVA-Dunnet's Test)

* significantly different from LPS at $p < 0.05$; ANOVA-Dunnet's Test)

* significantly different from LPS at p < 0.05; ANOVA-Dunnet's Test)

* significantly different from LPS at $p < 0.05$; ANOVA-Dunnet's Test)

* significantly different from LPS at p < 0.05; ANOVA-Dunnet's Test)

ANTI-INFLAMMATORY FORMULATIONS AND USES THEREOF INCLUDING A COMBINATION OF PALMITOYLETHANOLAMIDE AND PLANT-BASED POLYPHENOLS

CROSS-REFERENCE TO RELATED APPLICATIONS

This application claims priority to, and the benefit of, U.S. provisional application entitled "ANTI-INFLAMMATORY FORMULATIONS AND USES THEREOF INCLUDING A COMBINATION OF PALMITOYLETHANOLAMIDE AND PLANT-BASED POLYPHENOLS" having Ser. No. 62/685,060, filed Jun. 14, 2018, the contents of which are incorporated by reference in their entirety.

TECHNICAL FIELD

The present disclosure generally relates to anti-inflammatory formulations.

BACKGROUND

Palmitoylethanolamide (PEA) is an endogenous fatty acid amide belonging to the family of the N-acylethanolamines (NAEs) that exerts significant anti-inflammatory, analgesic properties and acts as a neuroprotective mediator (Impellizzeri et al., 2014). Impellizzeri et al. (2013) observed a potent analgesic and anti-inflammatory effects of PEA combined with luteolin in collagen-induced arthritis (CIA) mouse model. Other publications elucidate the efficacy of PEA as a neuroprotective in central nervous system pathologies (Cordaro et al., 2016; Parrela et al., 2016), as well as in several other diseases and inflammatory states such as irritable bowel syndrome (IBS) (Cremon et al., 2017), endometriosis (Di Paola et al. 2016) and skin inflammation (Cerrato et al., 2010; Vaia et al., 2016). The beneficial effects of quercetin (Chuang et al., 2010; Karuppagounder et al., 2016), curcumin (Kocaadam and Banlier, 2017), and resveratrol (Karuppagounder et al., 2014) among others, has been extensively reviewed and demonstrated in in vitro and in vivo models of inflammation. However, the combination of PEA with other polyphenols and natural compounds has been poorly investigated, with only a few reports on combined treatment and lack of evidence of synergistic effect. Considering the relevance of synergistic treatments to maximize response while optimizing the dosage of each compound, reformulation of existing products into combinations with higher therapeutic/prophylactic effect is essential.

There remains a need for improved anti-inflammatory formulations that overcome the aforementioned deficiencies.

SUMMARY

In various aspects, formulations and methods are provided that overcome the aforementioned deficiencies. Pharmaceutical and nutraceutical formulations are provided containing comprising an effective amount of (i) palmitoylethanolamide or a derivative thereof, and (ii) one or more small-molecule polyphenols or derivatives thereof. The pharmaceutical and nutraceutical formulations have been found to be effective to alleviate one or more causes or symptoms of inflammation when administered in an effective amount to a subject in need thereof. In some aspects, a first ratio of (i) a mass of the palmitoylethanolamide or derivative thereof in the formulation to (ii) a mass of the one or more small-molecule polyphenols or derivatives thereof in the formulation is about 0.25 to about 2.5. The formulations can be effective and suitable for humans as well as for non-human mammals and the like such as a dog, a cat, or a horse.

Methods are also provided for treating or alleviating one or more causes or symptoms of inflammation in a subject in need thereof by administering a formulation described herein. The method can include administering an effective amount of (i) palmitoylethanolamide or a derivative thereof and (ii) one or more small-molecule polyphenols or derivatives thereof to alleviate the one or more causes or systems of inflammation in the subject. In some aspects, the administration includes administering palmitoylethanolamide and one or both of quercetin and curcumin.

The pharmaceutical and nutraceutical formulations described herein, when administered in an effective amount, are effective against inflammation. For example, they can be effective against one or more causes or symptoms of the inflammation such as pain, swelling, stiffness, tenderness, redness, warmth, elevated inflammatory cytokines or other markers of inflammatory disease or a combination thereof. Because of the effectiveness of the formulations, in some aspects the therapeutically effective amount is less than a therapeutically effective amount of the otherwise same formulation except without the one or more small-molecule polyphenols or derivatives thereof. For example, in some aspects, the effective amount is less than 80% of an effective amount of the otherwise same formulation except without the one or more small-molecule polyphenols or derivatives thereof.

In some aspects formulation is a topical formulation; and the topical formulation is selected from the group consisting of a cream, an ointment, a salve, a spray, a gel, a lotion, an emulsion, a liquid, and a transdermal patch. The topical formulation can further include one or more chemical penetration enhancers, oils, lipids, membrane permeability agents, membrane transport agents, emollients, surfactants, stabilizers, or a combination thereof.

In some aspects, the formulation is an enteral formulation; and the enteral formulation is selected from the group consisting of tablets, capsules, solutions, suspensions, syrups, lozenges, and dry powders. The enteral formulation can further include one or more diluents, preservatives, binders, lubricants, disintegrators, swelling agents, fillers, stabilizers, or a combination thereof.

Various small molecular polyphenols have been found to be effective in combination with palmitoylethanolamide or a derivative thereof. In some aspects, the small molecule polyphenol is selected from the group consisting of rutin, quercetin, daidzein, daidzin, genistein, myricetin, hesperidin, neohesperidin, hesperetin, naringin, naringenin, curcumin, desmethoxycurcumin, bis-demethoxycurcumin, tetrahydrocurcumin, astragalin, kaempferol, resveratrol apigenin, delphinidin, delphin, peonidin, peonin, petunin, malvidin, cyanidin, pelargonidin, caffeic acid, chlorogenic acids, catechin, epicatechin, epigallocatechin gallate, ferulic acid, boswellic acids, rosmarinic acid, ellagic acid, p-coumaric acid, green tea polyphenols, and derivatives thereof. In some aspects the formulation include palmitoylethanolamide and one or both of quercetin and curcumin as these combinations have been found to be particularly effective at alleviating one or more causes and/or symptoms of inflammation.

Other systems, methods, features, and advantages of anti-inflammatory formulations will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1A:
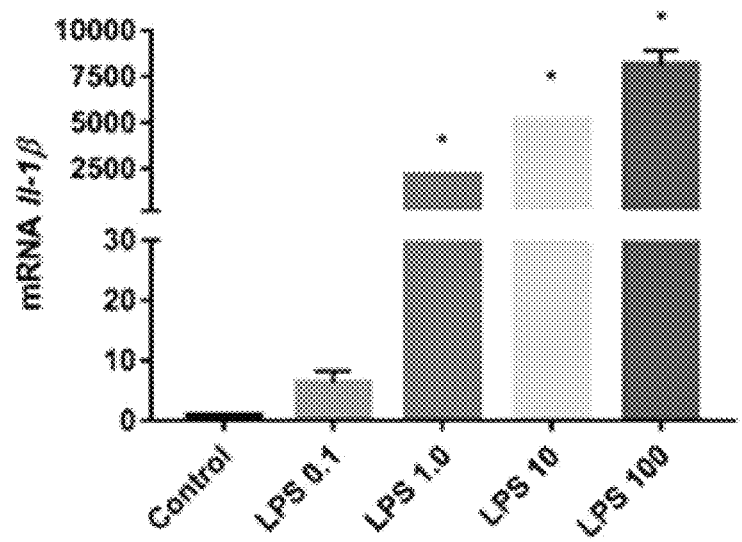
FIGS. 1A-1D show the effect of LPS activation (ng/mL) and anti-inflammatory activity of PEA (2.0 mg/L) in murine RAW264.7 macrophages in (FIG. 1A, FIG. 1C) II-1β and (FIG. 1B, FIG. 1D) Cox-2 expressions.
Figure 1B:
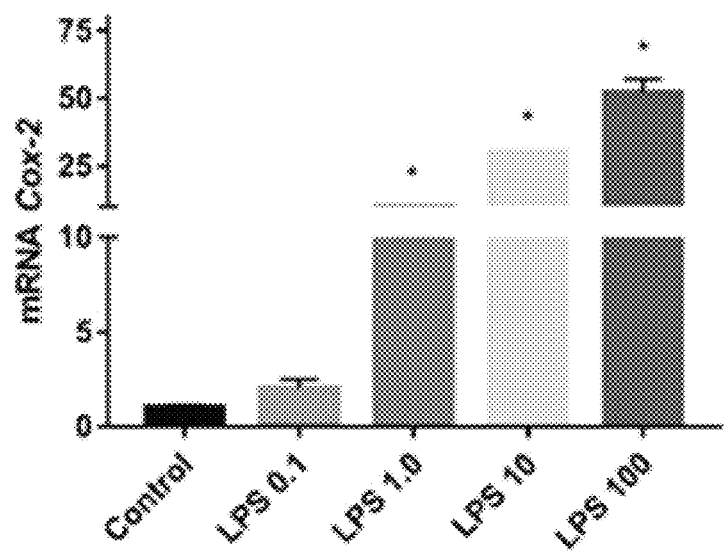
Figure 1C:
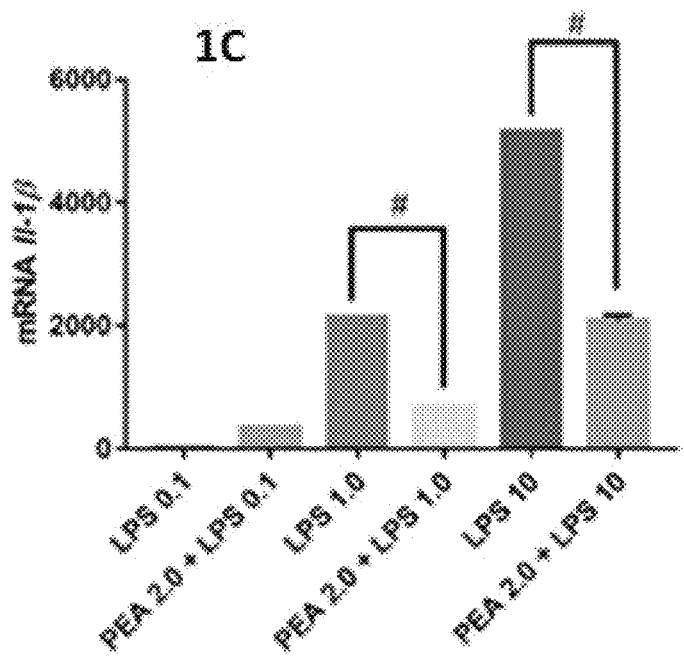
Figure 1D:
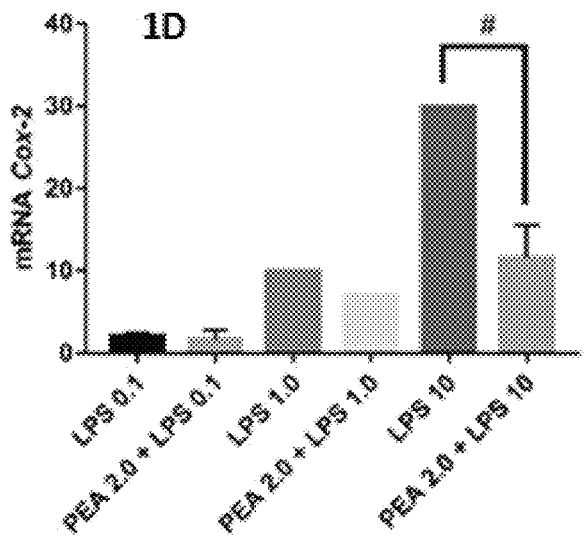
Figure 2A:
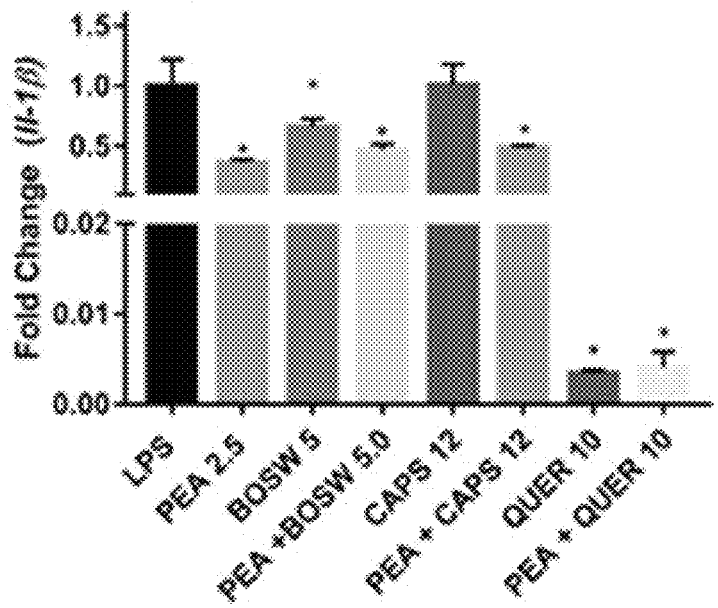
FIGS. 2A-2F show mRNA expression of LPS-activated (10 ng/mL) murine macrophages (RAW264.7) treated with PEA, Boswellia serrata extract, capsaicin, quercetin, curcumin and ibuprofen, alone or in combinations for 9 h.
Figure 2B:
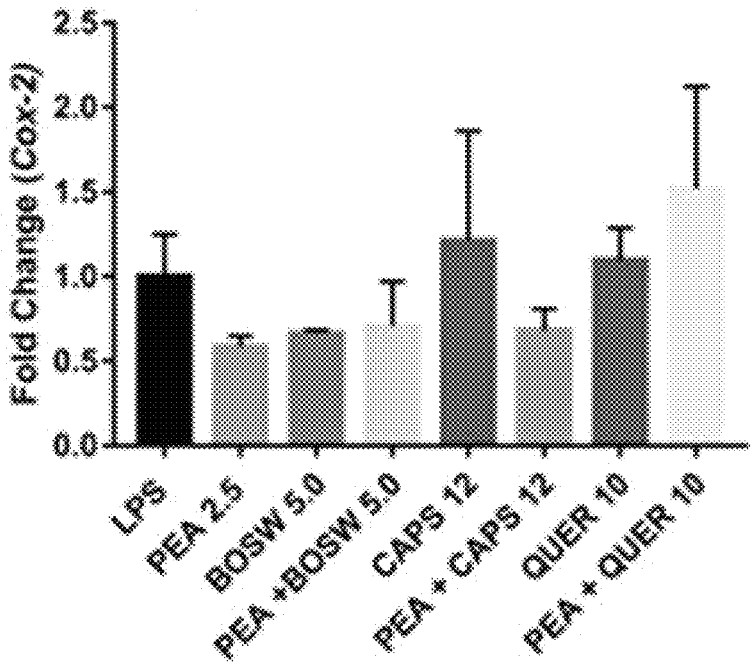
Figure 2C:
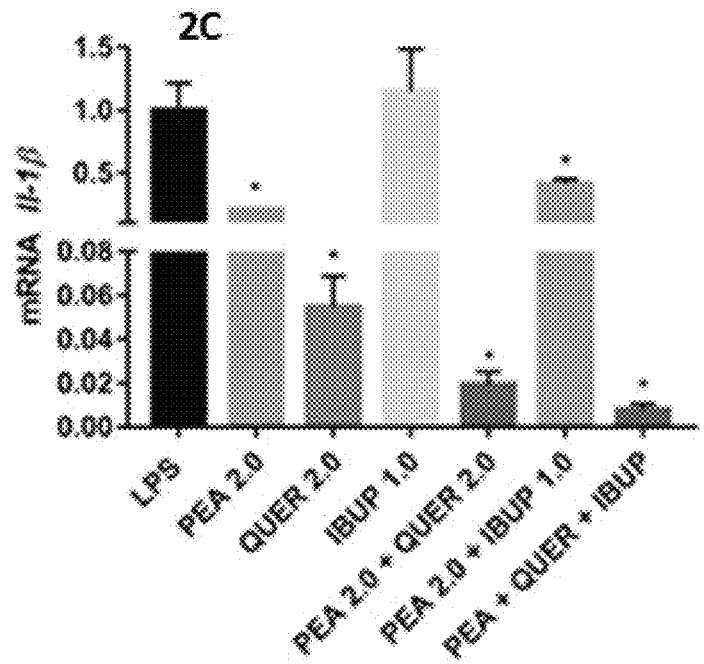
Figure 2D:
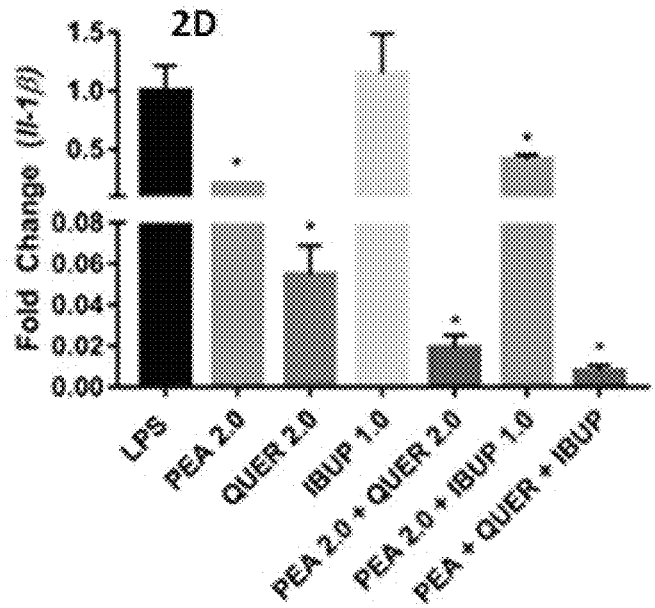
Figure 2E:
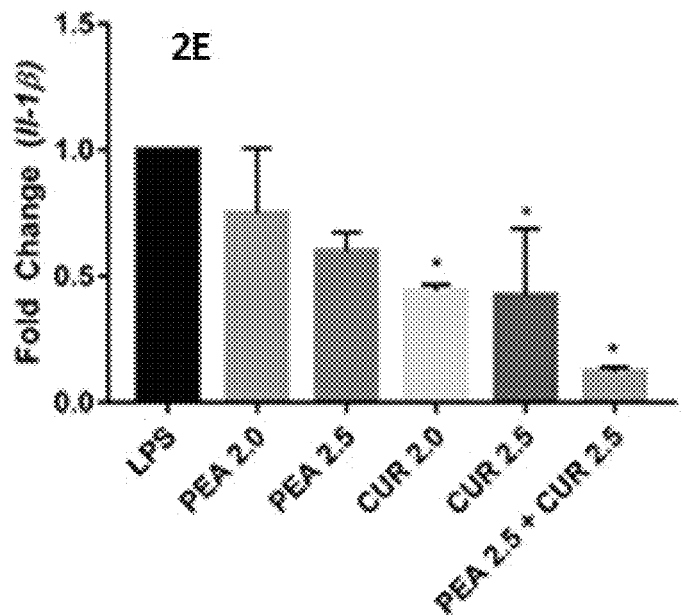
Figure 2F:
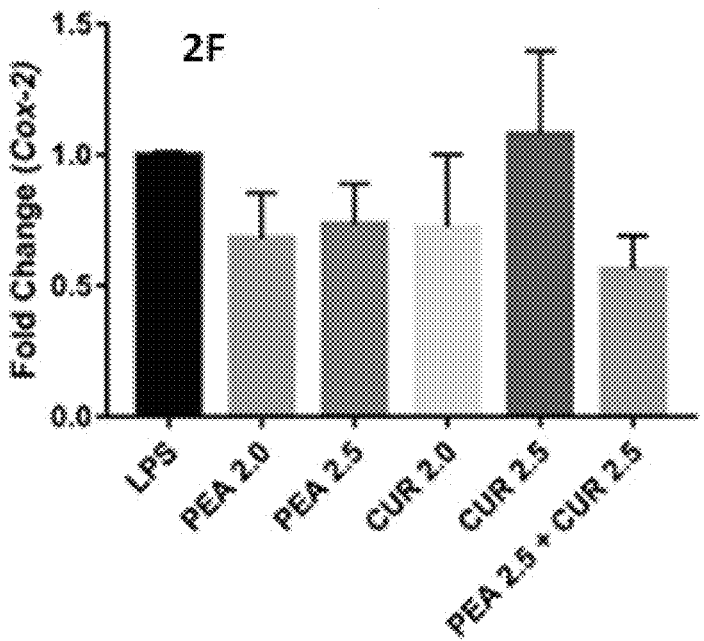
Figure 3A:
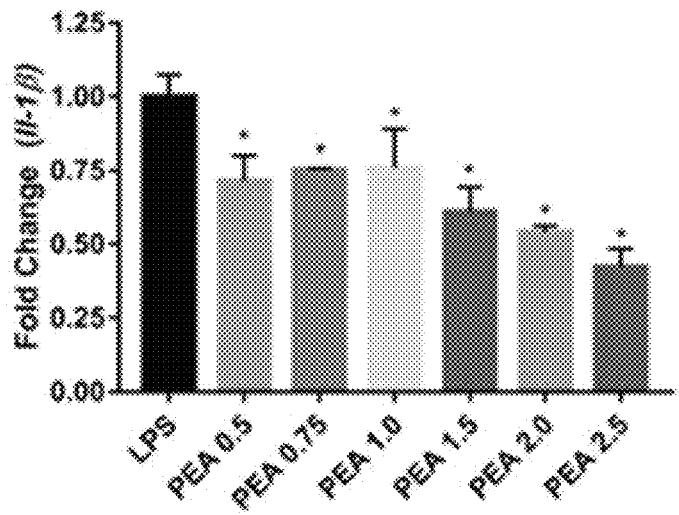
FIGS. 3A-3F show mRNA expression of LPS-activated (10 ng/mL) murine macrophages (RAW264.7) treated with PEA (a and b), quercetin (c and d) and curcumin (e and f) for 9 hours.
Figure 3B:
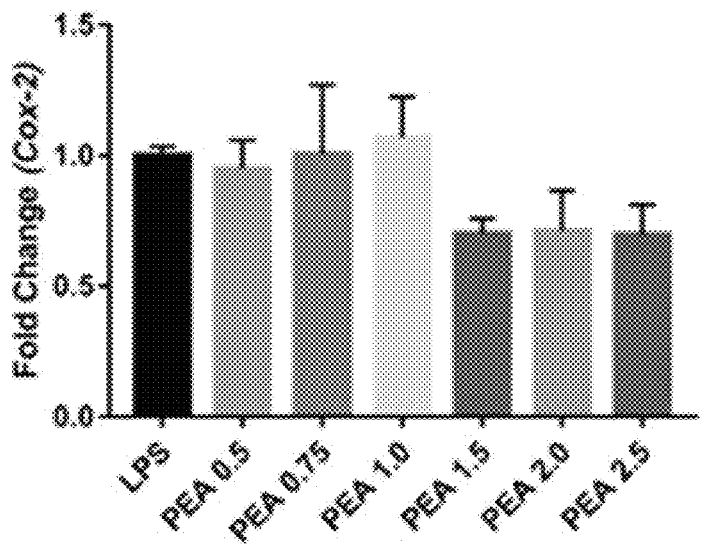
Figure 3C:
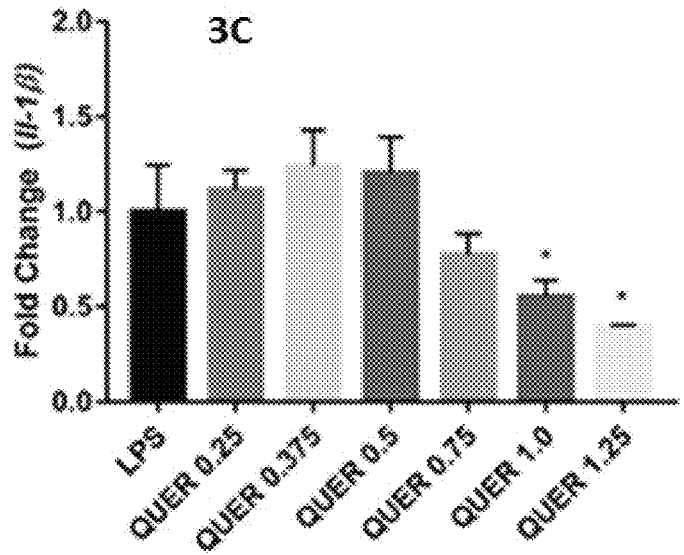
Figure 3D:
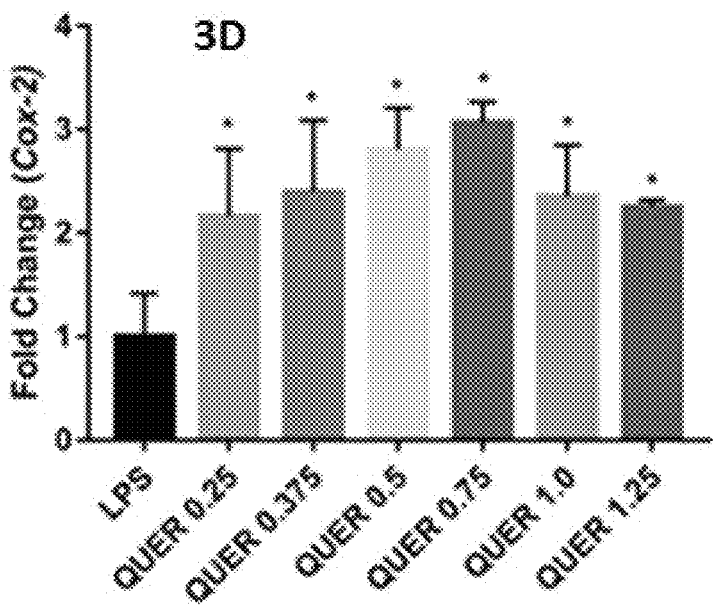
Figure 3E:
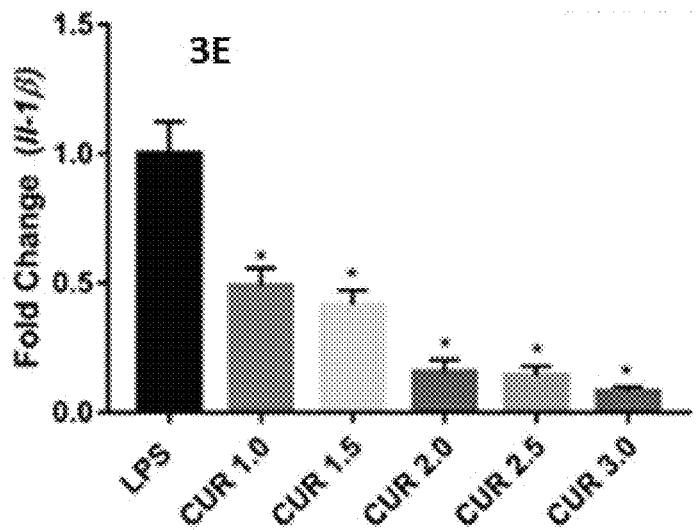
Figure 3F:
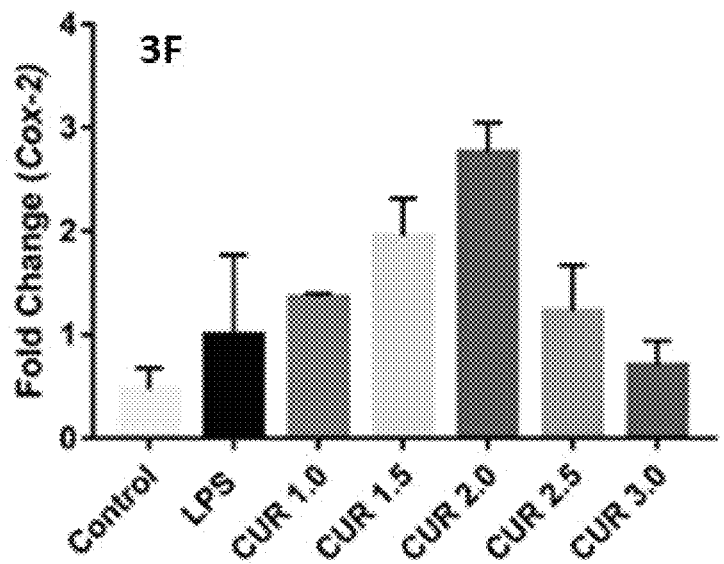
Figure 4A:
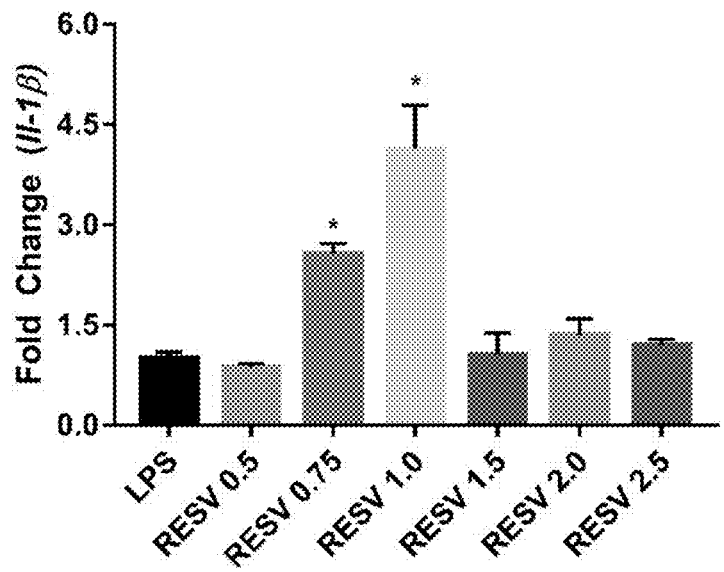
FIGS. 4A-4B show mRNA expression of LPS-activated (10 ng/mL) murine macrophages (RAW264.7) treated with resveratrol for 9 hours.
Figure 4B:
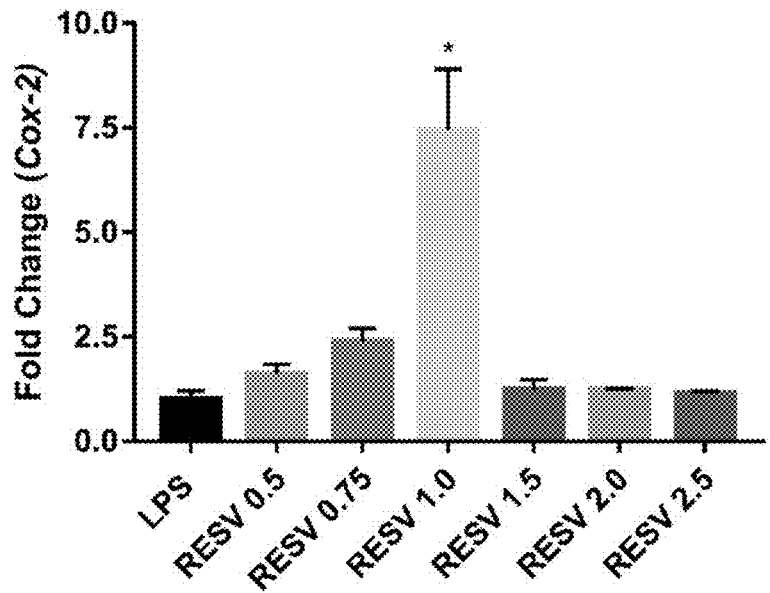

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of organic chemistry, pharmacology, and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x, greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The terms "subject" or "patient", as used herein, refer to any organism to which the active agents and compositions may be administered, e.g., for experimental, therapeutic, diagnostic, and/or prophylactic purposes. Typical subjects include animals (e.g., mammals such as mice, rats, rabbits, non-human primates, and humans).

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the inflammation of a subject by administration of an anti-inflammatory agent even though such agent may not treat the underlying cause of the inflammation.

The term "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease, support of a physiological structure or function, in the enhancement of desirable physical or mental development and conditions in an animal or human, or in the provision of medical or health benefits as a food or liquid or as a supplement that can either be taken independent of or when added to a food or liquid.

"Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, intraarticularly, subcutaneously, subjunctivally, by injection, and by infusion "Topical administration", as used herein, means the non-invasive administration to the skin, orifices, or mucosa. Topical administrations can be administered locally, i.e., they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

"Enteral administration", as used herein, means administration via absorption through the oral, buccal, sublingual and/or gastrointestinal tract. Enteral administration can include oral and sublingual administration, gastric administration, or rectal administration.

"Pulmonary administration", as used herein, means administration into the lungs by inhalation or endotracheal administration. As used herein, the term "inhalation" refers to intake of air to the alveoli. The intake of air can occur through the mouth or nose.

The terms "sufficient" and "effective", as used interchangeably herein, refer to an amount (e.g., mass, volume, dosage, concentration, and/or time period) needed to achieve one or more desired result(s). A "therapeutically effective amount" is at least the minimum concentration required to effect a measurable improvement or prevention of any symptom or a particular condition or disorder, to effect a measurable enhancement of life expectancy, or to generally improve patient quality of life. The therapeutically effective amount is thus dependent upon the specific biologically active molecule and the specific condition or disorder to be treated.

The term "pharmaceutically acceptable", as used herein, refers to compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the U.S. Food and Drug Administration. A "pharmaceutically acceptable carrier", as used herein, refers to all components of a pharmaceutical formulation that facilitate the delivery of the composition in vivo. Pharmaceutically acceptable carriers include, but are not limited to, diluents, oils, lipids, phospholipids, salts, esters, preservatives, binders, lubricants, disintegrators, swelling agents, fillers, stabilizers, and combinations thereof.

The term "pharmaceutically acceptable carrier" refers to a pharmaceutically acceptable carrier, penetration enhancer, salt, lipid or binding agent. In various embodiments, the pharmaceutically acceptable counter ion is a pharmaceutically acceptable ion, fatty acid, triglyceride, fatty acid ester. Lipid-based formulations (including oils, tinctures, powdered oils, emulsions, micelles, liposomes, nanoparticles and softgel capsules) containing can be made with any of a variety of lipids. Nonlimiting examples include (i) fatty acids, e.g., stearic acid; (ii) phospholipids, for example, phosphoglycerides, e.g., phosphatidyl choline, phosphatidylserine, phosphatidylethanolamine; (iii) amphiphilic lipids and polymers (iv) edible fats and oils, especially healthful oils, e.g., vegetable oils, coconut oil, palm oil, algal oil, olive oil, canola oil, fish oil; (iv) triacylglycerols; (vi) mixtures of any of these and/or other lipids and derivatives, e.g., essential oils or distillates from citrus, rosemary, turmeric, ginger or other fruits, herbs or spices, oils or distillates from plants of the Cannabaceae family; (vii) pharmaceutically acceptable salts, hydrates, polymers, and conjugates thereof, e.g. sorbitan ethylene oxide/propylene oxide copolymers (Polysorbate 20, Polysorbate a60, Polysorbate 80)) may be particularly useful. Other useful lipids include lecithin from soy or sunflower, (a mixture of glycolipids, triglycerides, and phospholipids). The term "pharmaceutically acceptable salt(s)" refers to salts, esters, or other covalently bound groups that may be acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The term "derivative," as used herein" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. For example, where the reference compound is a polyphenol, the derivatives can include aglycones and glycosides of the polyphenol. Derivatives can also include analogues of the reference compound, conjugates of the reference compound, and oligomers and polymers of the reference compound. When the reference compound is a polyphenol, the derivatives can include aglycones and glycosides of the polyphenol.

Pharmaceutical Formulations

Applicants have found that certain combinations of palmitoylethanolamide and small-molecule polyphenols exhibit a synergistic effect in treating or alleviating inflammation in a subject in need thereof. The combinations are demonstrated to have markedly increased therapeutic or prophylactic effect as compared to either active agent individually. In some aspects, the therapeutically effective amount is less than a therapeutically effective amount of the otherwise same formulation except without the one or more small-molecule polyphenols or pharmaceutically acceptable salts thereof. In some aspects, the therapeutically effective amount is less than 90%, less than 80%, less than 70%, less than 60%, or less than 55% of a therapeutically effective amount of the otherwise same formulation except without the one or more small-molecule polyphenols or pharmaceutically acceptable salts thereof. In some aspects, a first ratio of (i) a mass of the palmitoylethanolamide or derivative thereof in the formulation to (ii) a mass of the one or more small-molecule polyphenols or derivative thereof in the formulation is about 3.0 to about 7.0, about 0.25 to about 5.0, about 0.25 to about 3.5, about 0.25 to about 2.5. about 0.5 to about 2.0, about 0.5 to about 1.5, about 0.5, about 1.0, about 1.5, or about 2.0, about 2.5, or about 5.0. The formulations can include a pharmaceutical acceptable carrier. In some aspects, the formulations include no added carrier. In some aspects, the formulation contains two or more small-molecule polyphenols or derivatives thereof. In some aspects, a mass ratio of a first small-molecule polyphenol to a second small-molecule polyphenol is about 1:1 to about 3:1 or about 2:1.

The formulations and methods can include palmitoylethanolamide (IUPAC name N-(2-Hydroxyethyl)hexadecanamide). Palmitoylethanolamide (PEA) is an endogenous fatty acid amide. PEA has been demonstrated to bind to a receptor in the cell-nucleus (a nuclear receptor) and exerts a great variety of biological functions related to chronic pain and inflammation. PEA has a structure according to the following formula:

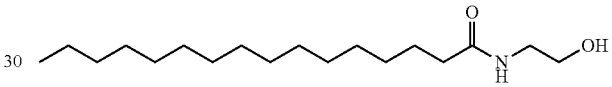

The formulations and methods can include a derivative of PEA.

Applicants have found that PEA has a synergistic effect when administered with certain small-molecule polyphenols. Small-molecule polyphenols can include polyphenols having at least two hydroxyl groups and having a molecular weight of up to 1200 g/mol, about 1000 g/mol, 900 g/mol, 800 g/mol, 700 g/mol, 600 g/mol, about 500 g/mol, about 400 g/mol, or less. In some aspects, the small molecule polyphenol is selected from the group consisting of rutin, quercetin, daidzein, daidzin, genistein, myricetin, hesperidin, neohesperidin, hesperetin, naringin, naringenin, curcumin, desmethoxycurcumin, bis-demethoxycurcumin, tetrahydrocurcumin, astragalin, kaempferol, resveratrol apigenin, delphinidin, delphin, peonidin, peonin, petunin, malvidin, cyanidin, pelargonidin, caffeic acid, chlorogenic acids, catechin, epicatechin, epigallocatechin gallate, ferulic acid, boswellic acids, rosmarinic acid, ellagic acid, p-coumaric acid, green tea polyphenols, and derivatives thereof. The small molecule polyphenol may be in aglycone or glucoside form, or as a monomer, oligomer or polymer. In some aspects, the small-molecule polyphenol includes one or both of quercetin and curcumin or a derivative thereof.

The formulations described herein contain an effective amount of (i) palmitoylethanolamide or a derivative thereof and (ii) one or more small molecule polyphenols or derivatives thereof (collectively referred to as the "active agents"). In some aspects, no carrier is needed as the polyphenol can function as a carrier. In some aspects, the formulations can also include a pharmaceutical carrier appropriate for administration to an individual in need thereof. The formulations can be administered enterally (e.g. through the gut or oral), intraarticularly, or topically (e.g., to the skin).

In some aspects, formulations described herein contain a combination of (i) palmitoylethanolamide or a derivative thereof, (ii) curcumin or a derivative thereof, and (iii) quercetin or a derivative thereof. In some aspects, the components in the formulation are present at a mass ratio of about (i) 4 mg to 6 mg of palmitoylethanolamide or a derivative thereof to (ii) 0.5 to 2.5 mg curcumin or a derivative thereof, and (iii) 0.5 mg to 1.5 mg quercetin or a derivative thereof. In some aspects, a mass ratio of (i) the palmitoylethanolamide or derivative thereof to (ii) the curcumin or derivative thereof is from about 1:1 or about 5:3 and up to about 5:2, about 5:1, or about 6:1. In some aspects, a mass ratio of (i) the palmitoylethanolamide or derivative thereof to (ii) the quercetin or derivative thereof is from about 1:1 or about 5:3 and up to about 5:2, about 5:1, or about 6:1.

Topical Formulations

The active agents can be formulated for topical administration. Suitable dosage forms for topical administration include creams, ointments, salves, sprays, gels, lotions, emulsions, liquids, and transdermal patches. The formulation may be formulated for transmucosal, transepithelial, transendothelial, or transdermal administration. The compositions contain one or more chemical penetration enhancers, membrane permeability agents, membrane transport agents, emollients, surfactants, stabilizers, and combination thereof.

In some embodiments, the active agents can be administered as a liquid formulation, such as a solution or suspension, a semi-solid formulation, such as a lotion or ointment, or a solid formulation. In some embodiments, the active agents are formulated as liquids, including solutions and suspensions, such as eye drops or as a semi-solid formulation, such as ointment or lotion for topical application to the skin, to the mucosa, such as the sublingual or buccal (mouth), the eye, nasal cavity vaginally or rectally. The formulation may contain one or more excipients, such as emollients, surfactants, emulsifiers, penetration enhancers, and the like.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, algal oil, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, guar gum, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of the active agents in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopolhomopolymers and copolymers; and combinations thereof. Suitable solvents in the liquid vehicle include, but are not limited to, diglycolmonoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

Preservatives can be used to prevent the growth of fungi and microorganisms. Suitable antifungal and antimicrobial agents include, but are not limited to, benzoic acid, butylparaben, butylated hydroxytoluene, plant-derived essential oils, ethyl paraben, methyl paraben, propylparaben, sodium benzoate, sodium propionate, benzalkonium chloride, benzethonium chloride, benzyl alcohol, cetylpyridinium chloride, phenol, phenylethyl alcohol, rosemary, In certain embodiments, it may be desirable to provide continuous delivery of one or more active agents to a patient in need thereof. For topical applications, repeated application can be done or a patch can be used to provide continuous administration of the PEA and polyphenols over an extended period of time.

Enteral Formulations

The active agents can be prepared in enteral formulations, such as for oral administration. Suitable oral dosage forms include tablets, capsules, solutions, suspensions, syrups, lozenges, and dry powders. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations are prepared using pharmaceutically acceptable carriers. As generally used herein "carrier" includes, but is not limited to, lipids, phospholipids, salts, emulsifiers, excipients, diluents, preservatives, binders, lubricants, disintegrators, swelling agents, fillers, stabilizers, and combinations thereof. Polymers used in the dosage form include hydrophobic or hydrophilic polymers and pH dependent or independent polymers. Preferred hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. Carrier also includes all components of the coating composition which may include plasticizers, pigments, colorants, stabilizing agents, and glidants.

Formulations can be prepared using one or more pharmaceutically acceptable excipients, including diluents, preservatives, binders, lubricants, disintegrators, swelling agents, fillers, stabilizers, and combinations thereof.

Controlled release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and controlled release dosage forms of tablets, capsules, and granules. These references provide information on carriers, materials, equipment and process for preparing tablets and capsules and controlledrelease dosage forms of tablets, capsules, and granules.

The active agents may be coated, for example to control release once the particles have passed through the acidic environment of the stomach. Examples of suitable coating materials include, but are not limited to, modified starch or cellulose polymers such as cellulose acetate phthalate, hydroxypropyl cellulose, hydroxypropyl methylcellulose, hydroxypropyl methylcellulose phthalate and hydroxypropyl methylcellulose acetate succinate; lipids such as stearic acid, phospholipids, oils, and the like; cosolvents such as ethanol, glycerin, glycols and water; polyvinyl acetate phthalate, acrylic acid polymers and copolymers, and methacrylic resins that are commercially available under the trade name EUDRAGIT® (Roth Pharma, Westerstadt, Germany), zein, shellac, and other polysaccharides. Additionally, the coating material may contain conventional carriers such as plasticizers, pigments, colorants, glidants, stabilization agents, pore formers and surfactants.

Coatings may be formed with a different ratio of water soluble polymer, water insoluble polymers and/or pH dependent polymers, with or without water insoluble/water soluble non polymeric excipient, to produce the desired release profile. The coating is either performed on dosage form (matrix or simple) which includes, but not limited to, tablets (compressed with or without coated beads), capsules (with or without coated beads), beads, particle compositions, powders, liquids, oils, gels, emulsions, micelles or liposomes Optional pharmaceutically acceptable carriers include, but are not limited to, lipids, phospholipids, salts, emulsifiers, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

Dry Powder Formulations

Dry powder formulations are finely divided solid formulations containing one or more active agents which are suitable for oral administration. Dry powder formulations can be taken independently or can be added, for instance, to a liquid or food product for ingestion. Dry powder formulations include one or more active agents. Such dry powder formulations can be administered orally to a patient containing one or more active agents. The active agents can be in combination with a pharmaceutically acceptable carrier.

The pharmaceutical carrier may include a bulking agent, such as carbohydrates (including monosaccharides, polysaccharides, and cyclodextrins), polypeptides, amino acids, and combinations thereof. Suitable bulking agents include dietary fiber, fructose, galactose, glucose, lactitol, lactose, maltitol, maltose, maltodextrin, mannitol, starches, sucrose, trehalose, xylitol, hydrates thereof, and combinations thereof. The pharmaceutical carrier may include any of those previously stated.

Methods of Treating or Alleviating Inflammation

Various methods are provided for treating or alleviating one or more symptoms of inflammation in a subject in need thereof. The methods can include administering a therapeutically effective amount of (i) palmitoylethanolamide or a derivative thereof and (ii) one or more small molecule polyphenols or a derivative thereof to alleviate one or more systems of the inflammation in the subject. The methods can include administering a pharmaceutical formulation described herein to the subject.

In some aspects, a therapeutically effective amount includes from about 1 mg or about 2.5 mg of active agents and up to about 25 mg or 50 mg of active agents per pound of body weight. In some aspects, the methods include administering a first number of loading dosages, wherein the loading dosage is about 5 mg or about 7.5 mg of active agents and up to about 15 mg, 20 mg, or 25 mg of active agents per pound of body weight. In some aspects, after a loading period, the methods include administering a maintenance dosage of about 2.5 mg to about 7.5 mg of active agents per pound of body weight. Therapeutically effective amounts can, in some aspects, include about 2.5-50 mg, about 2.5-25 mg, about 2.5-15 mg, about 2.5-7.5 mg, about 7.5-15 mg, about 5 mg, about 10 mg, about 15 mg, or about 20 mg per pound of body weight.

Inflammation may have different causes, including pathogens (germs) like bacteria, viruses or fungi, external injuries like scrapes or foreign objects, or the effects of chemicals or radiation. In some aspects, the inflammation is an acute inflammatory response to an injury or tissue damage. In some aspects, the inflammation arises from an inflammation-associated disorder, for example, osteoarthritis, rheumatoid arthritis, osteoarthritic joint pain, rheumatoid arthritic joint, joint pain, inflammatory pain, acute pain, chronic pain, cystisis, bronchitis, dermatitis. In some aspects, the inflammation may be part of a chronic age-related disease, for example, cardiovascular disease, neurodegenerative disease, liver disease, lung disease or kidney disease. The one or more symptoms of the inflammation can include pain, swelling, stiffness, tenderness, redness, warmth, elevated biomarkers related to disease states, such as cytokines, immune receptors, inflammatory markers, and a combination thereof. The methods provided herein can be effective to alleviate (completely or partially) one or more of the symptoms of inflammation.

Suitable subjects can include human and non-human subjects, e.g. mammals. In some aspects, the subjects include veterinary animals such as dogs, cats, horses, and the like.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Materials and Methods

Cell Cultures

RAW 264.7 murine macrophage cell line was purchased from American Type Culture Collection (ATCC-TIB71). Cells were cultured in high glucose Dulbecco's Modified Eagle Medium (DMEM) supplemented with stable glutamine (0.0584%) and sodium pyruvate (0.011%), 10% (v/v) heat-inactivated fetal bovine serum, and 1% (v/v) penicillin/streptomycin mix. Cells were maintained in an incubator at 37° C. with 5% CO2, and the medium was changed every two days. All assays were conducted in cells between the 3rd and the 15th passage. All treatments with PEA and other polyphenols were solubilized in dimethyl sulfoxide (DMSO) and further diluted in complete culture media immediately before use. LPS (10 ng mL-1) was used to induce inflammation in RAW 264.7 cultures.

Quantitative RT-qPCR

Murine RAW 264.7 macrophage cells (1×105 cells per well) were seeded in 12-well plates and incubated for 24 hours. Cells were pre-treated with Palmitoylethanolamide (PEA) and other compounds of interest for 1 hour and then lipopolysaccharide (LPS), a major activating agent of macrophages, was added for a final concentration of 10 ng·mL-1. Cells were then incubated for 8 hours. Negative control (culture media only) and positive (LPS) controls, as well as a Vehicle (DMSO at a maximal concentration of 0.2%)+LPS were also performed. Total RNA was extracted and purified using an RNeasy mini kit (QIAGEN, Venlo, Netherlands) according to the manufacturer's protocol. mRNA quality and quantification were assessed with NanoDrop® ND-1000 (NanoDrop Technologies, Wilmington, Del., USA). cDNA synthesis was performed with the iScript Reverse Transcription Supermix (Bio-Rad Laboratories, Hercules, Calif., USA) according to the manufacturer's protocol. RT-qPCR reactions were performed using iTaq Universal Probes Supermix (Bio-Rad Laboratories, Hercules, Calif., USA). mRNA expression cyclooxygenase-2 (Cox-2) and interleukin-1 beta (II-1β) were analyzed using beta-actin (Actb) as a reference gene. The levels of transcripts were calculated relative to the control group by the 2-ΔΔCt method.

Statistical Analysis

All data were analyzed by one-way analysis of variance (ANOVA) with Dunnet's or Sidak's posttest using GraphPad Prism 6.0 (GraphPad Software, La Jolla, Calif., USA). Data were considered significantly different when $p<0.05$. Combination Index (CI) analysis of free drug combination and isobolographic analysis were performed based on the Chou and Talalay method (Chou and Talalay 1984) using CompuSyn software (Version 1.0, Combo-Syn Inc., U.S.).

Results and Discussion

Testing Model Validity for LPS-Induced Inflammatory Response

Lipopolysaccharide (LPS) is known to activate cellular signals in macrophages since it is a component of the cell wall of gram-negative bacteria (Guha and Mackman, 2001). This compound is used to activate normal cells in vitro, as its activation produces various inflammatory mediators.

Macrophages play a significant role in immune reactions and are predominantly involved in the inflammatory response, representing a well-established model for studying inflammation (Murray and Wynn, 2011). Preliminary experiments aimed at optimizing LPS and PEA concentrations used in the RAW264.7 model (FIGS. 1A-1D). LPS exerted a dose-dependent effect on macrophage activation, whereas 1.0 ng/mL significantly increased the inflammatory response of both Il-1β and Cox-2. The concentration of 10 ng/mL was selected for use in the following experiments, as it presented significant inflammatory activity and is within the range found in published literature for this cell line (Mosser et al. 2008; Gabrielsson et al. 2017).

PEA at 2.0 mg/L was capable of significantly decrease the expression of the inflammatory cytokine Il-1β after 1.0-10 ng/mL LPS and at 10 ng/mL for Cox-2, indicating the effectiveness of the model and PEA treatment.

Screening of Possible Synergistic Compounds Against Inflammation in Murine Macrophages Cytokines/chemokines as well as cyclooxygenase 2 (Cox-2) are important targets for the modulation of the inflammatory response. As preliminary tests, several known anti-inflammatory compounds and botanicals were tested at different concentrations, alone or in combination with PEA. The expressions of Il-1p and Cox-2 was investigated and it is shown in FIGS. 2A-2F.

Treatment with *Boswellia serrata* and capsaicin showed significant reduction in the expression of IL-1β both alone and in combination with PEA, although the response was not as remarkable as the observed for other compounds such as quercetin and curcumin. Furthermore, the effective concentrations of quercetin and curcumin were lower than for *Boswellia serrata* and capsaicin, showing another potential advantage of the aforementioned compounds. Ibuprofen is a non-steroidal anti-inflammatory drug commonly used for treatment of pain and inflammation. The tested concentration of ibuprofen did not improve the inflammatory state of the cells and therefore was not further investigated.

Dose-Response Curves for Individual Compounds

The results obtained during the screening phase allowed the selection of a few compounds with prospective synergistic activity. Dose-response curves were generated based on treatment of cells with each compound alone. This data is necessary for generating the IC50 for each compound alone and to direct following experiments towards the optimal treatment concentration. Anti-inflammatory activity was observed for Il-1β, for which PEA alone was significantly effective at concentrations as low as 0.5 mg/L (FIGS. 2A-2B), reducing 28% of its expression. For this reason, this concentration was consistently used in the following experiments. Both quercetin and curcumin alone decreased inflammation starting at 1.0 mg/L at a dose-dependent manner. At 1.0 mg/L, these compounds reduced around 45% and 57% of IL-1β mRNA expression, respectively.

Resveratrol was also investigated as a potential combinational compound, but no downregulation of Il-1β or Cox-2 were observed for the compound alone (FIGS. 3A-3F).

Optimization of Combinations Between PEA and Phenolic Compounds

Figure 5A:
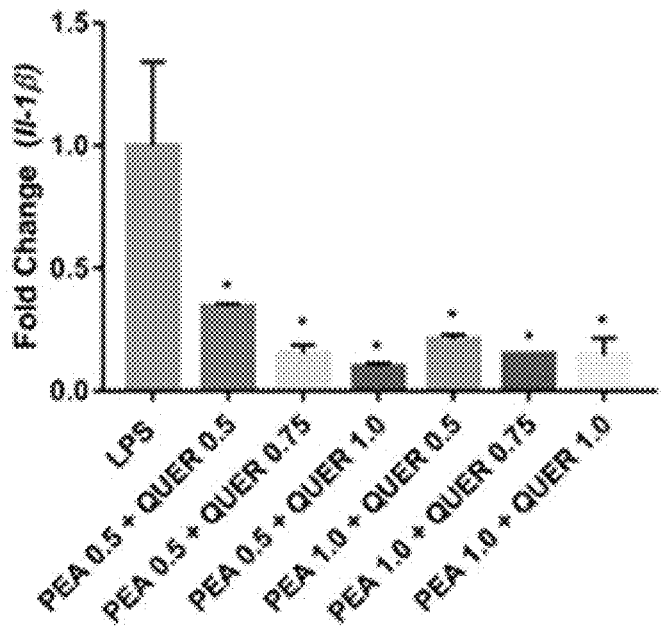
FIGS. 5A-5D show mRNA expression of LPS-activated (10 ng/mL) murine macrophages (RAW264.7) treated with different combinations of PEA-quercetin (FIGS. 5A-5B) and PEA-curcumin (FIGS. 5C-5D).
Figure 5B:
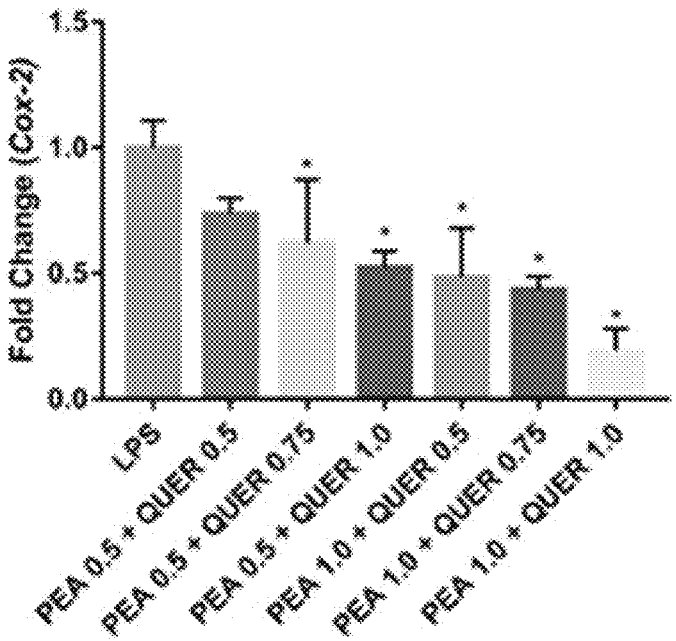
Figure 5C:
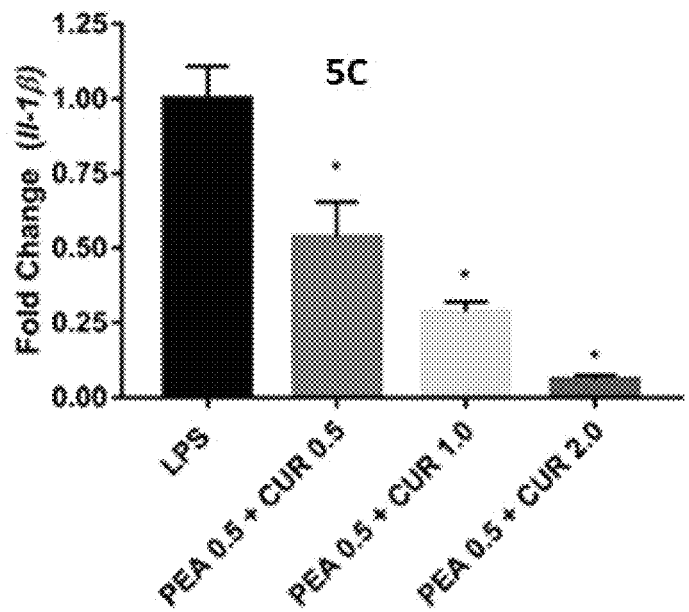
Figure 5D:
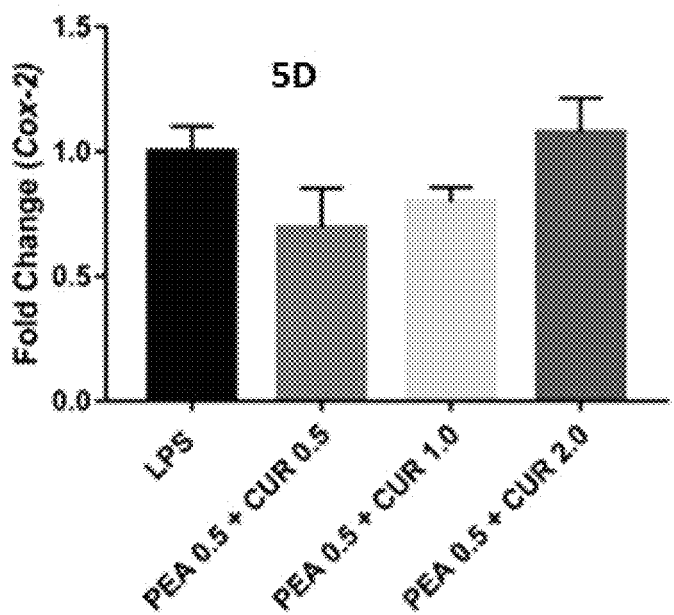

Compounds that showed significant anti-inflammatory effects were combined with PEA to investigate potential synergistic effects. Combinations were more potent in downregulating LPS-induced pro-inflammatory markers than compounds alone. As previously mentioned, PEA and quercetin can effectively reduce macrophage activation at concentrations of 0.5 mg/L and 1.0 mg/L, respectively. When combined, these compounds at 0.5 mg/L reduced more than 50% mRNA expression of IL-Iβ and around 30% of Cox-2 (FIGS. 5A-5B), indicating synergistic activity. PEA+curcumin also downregulated IL-1β at the lowest concentration tested (0.5 mg/L of each compound) (FIG. 5C), showing 46% reduction at that concentration and better effects at higher concentrations. No effect was observed for Cox-2.

Figure 6A:
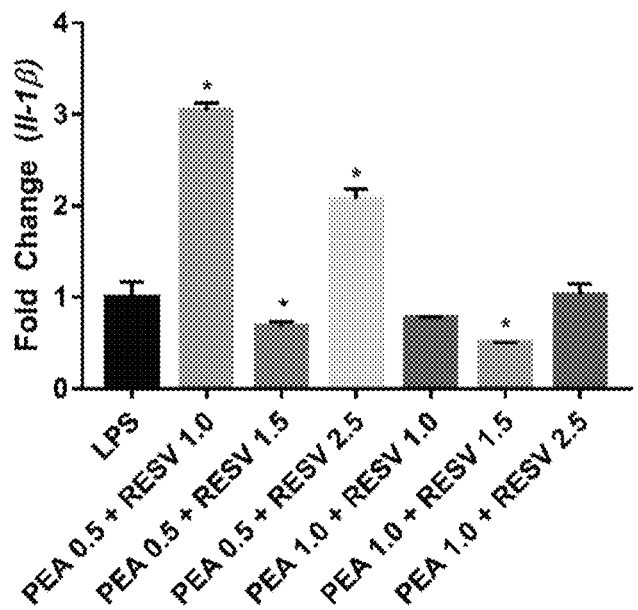
FIGS. 6A-6B show mRNA expression of LPS-activated (10 ng/mL) murine macrophages (RAW264.7) treated with different combinations of PEA-Resveratrol.
Figure 6B:
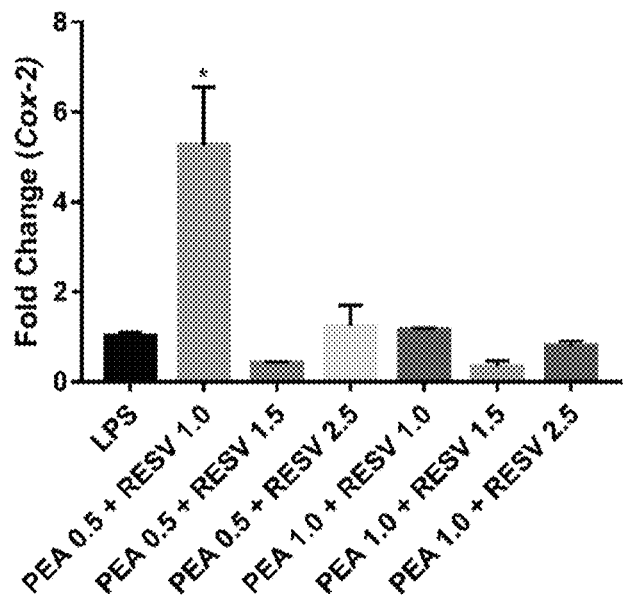

Although the anti-inflammatory activity of resveratrol has been widely described in the literature, this compound did not reduce mRNA expression of IL-1B and Cox-2 when used alone. When combined with PEA, the combinations PEA 0.5+RESV 1.5 and PEA 1.0+RESV 1.5 were significantly lower than the LPS control (FIG. 6).

Synergistic Interactions Between PEA and Selected Botanicals

Based on the individual dose-response curves and the different combinational experiments between compounds, it was determined that quercetin and curcumin were the compounds with stronger suggestion of synergistic effect when combined with PEA. To prove the suggested synergism, the Combination Index (CI) was calculated and the respective isobologram for each combination were generated. A CI<1 indicates that the concentrations producing a given effect in combination are lower than the expected concentrations from additivity and can therefore be interpreted as synergy (Chou and Talalay 1984).

Figure 7A:
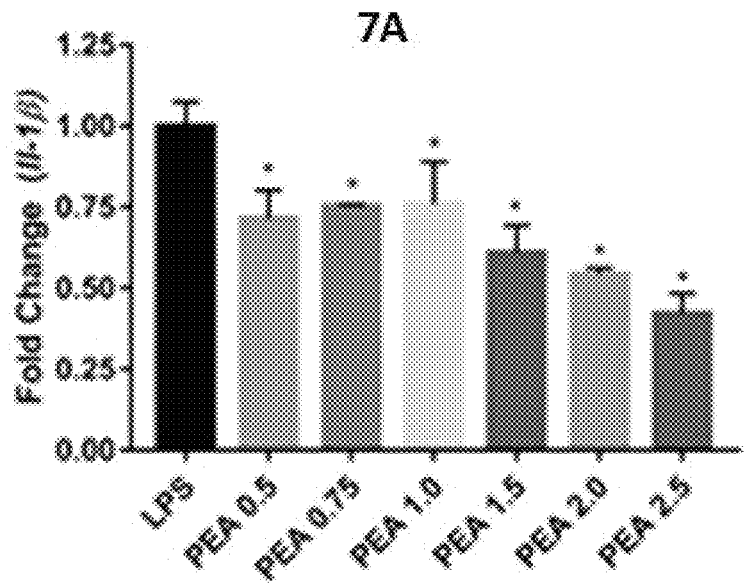
FIGS. 7A-7C show mRNA expression of LPS-activated (10 ng/mL) murine macrophages (RAW264.7) treated with PEA and quercetin alone (FIGS. 7A-7B) and their combinations (FIG. 7C).
Figure 7B:
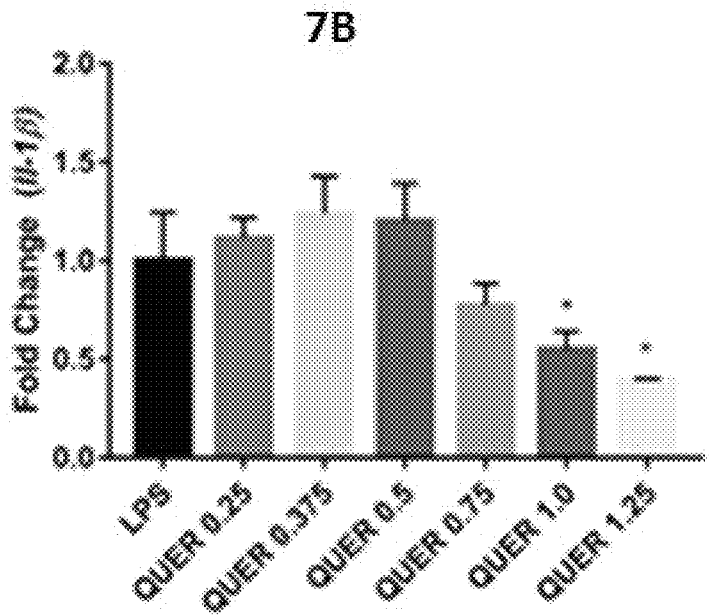
Figure 7C:
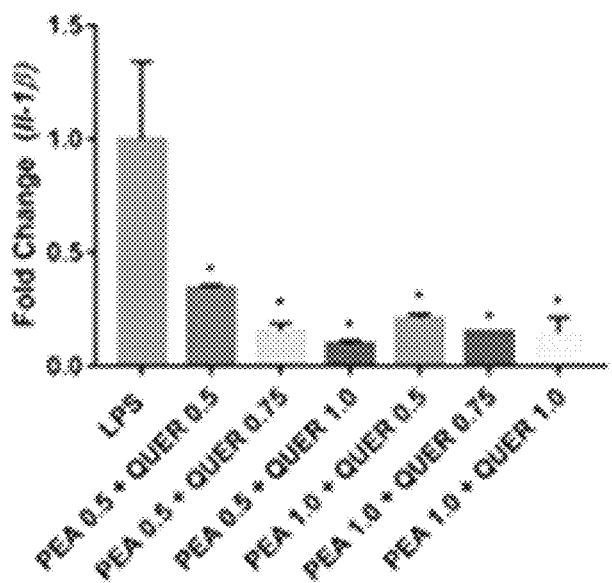
Figure 8:
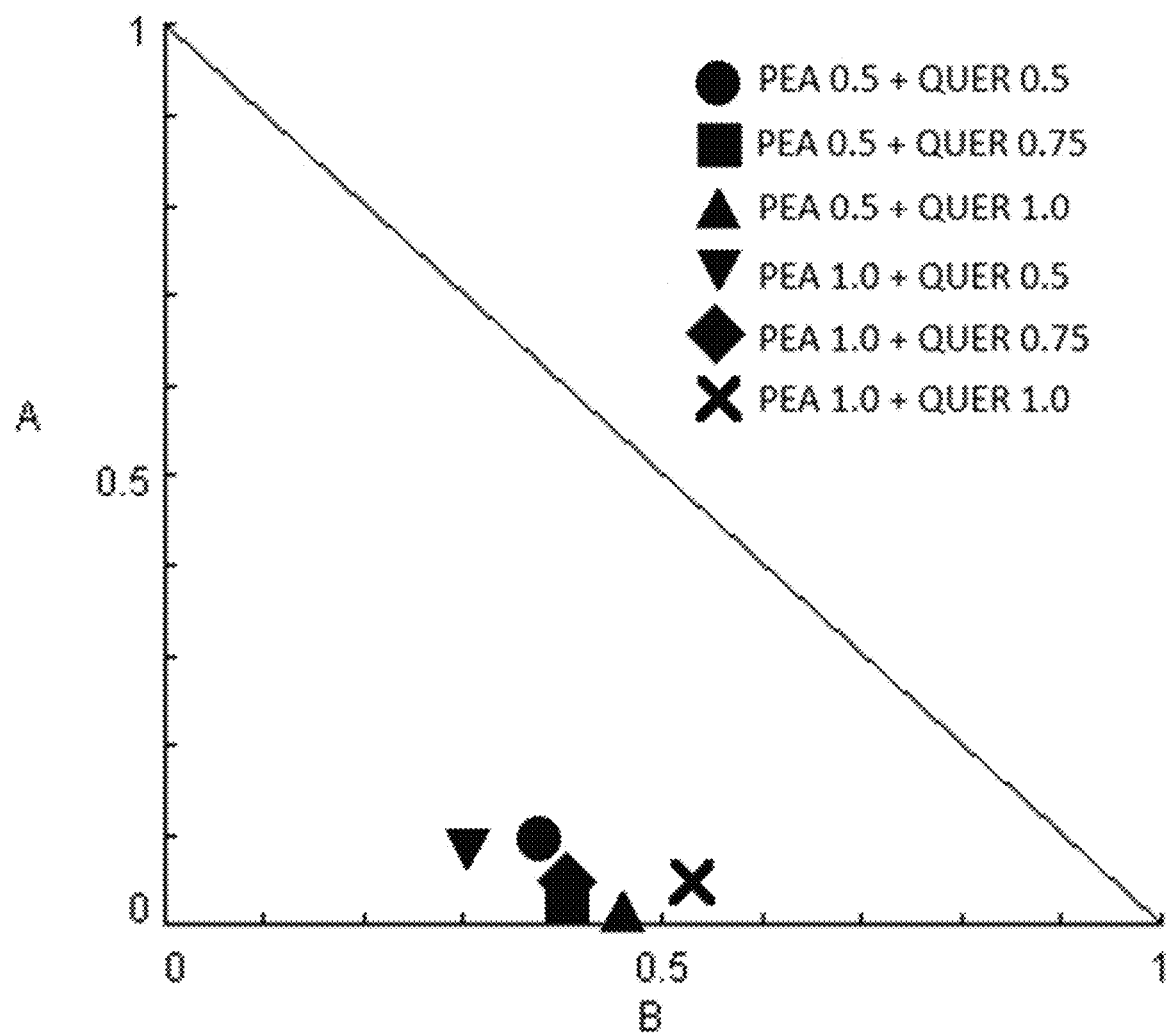
FIG. 8 shows Isobolographic analysis based on II-1β expression of murine macrophages (RAW264.4) cells treated for 9 h with PEA and quercetin alone, as well as their combinations. Isobologram was normalized to the IC50 of individual compounds.

FIGS. 7A-7C show the combination of PEA and quercetin was remarkably more effective than the compounds alone by reducing IL-1β to 34.5% of LPS control. Furthermore, the isobologram (FIG. 8) indicates all combinations between PEA and quercetin were synergistic, as all treatments fell under the additivity curve. The results of the combination index (CI) analysis (Table 1) show the strongest synergy is observed for PEA 1.0+QUER 0.5 mg/L, and all combinations had a CI<1.

TABLE 2

Combination Indexes (CI) for all testes combinations

| PEA + Quercetin | | PEA + Curcumin | |
|---|---|---|---|
| Combination concentrations | CI | Combination concentrations | CI |
| PEA 0.5 + QUER 0.5 | 0.4720 | PEA 0.5 + CUR 0.5 | 0.7468 |
| PEA 0.5 + QUER 0.75 | 0.4335 | PEA 0.5 + CUR 1.0 | 0.6972 |
| PEA 0.5 + QUER 1.0 | 0.4755 | PEA 0.5 + CUR 2.0 | 0.5574 |
| PEA 1.0 + QUER 0.5 | 0.3894 | — | — |
| PEA 1.0 + QUER 0.75 | 0.4551 | — | — |
| PEA 1.0 + QUER 1.0 | 0.5799 | — | — |

Figure 9A:
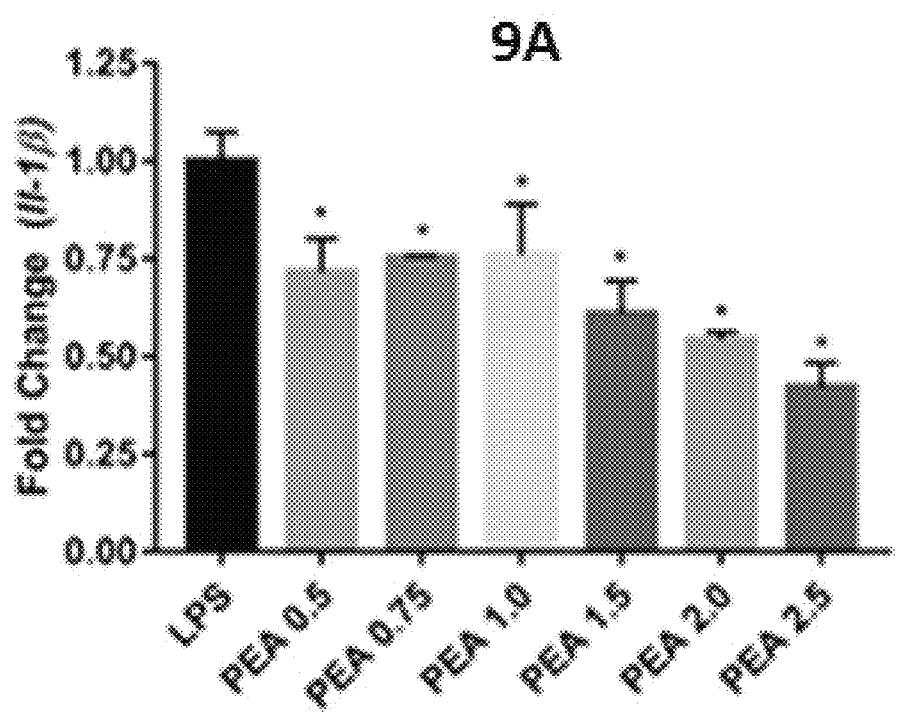
FIGS. 9A-9C show mRNA expression of LPS-activated (10 ng/mL) murine macrophages (RAW264.7) treated with PEA and curcumin alone (FIGS. 9A-9B) and their combinations (FIG. 9C).
Figure 9B:
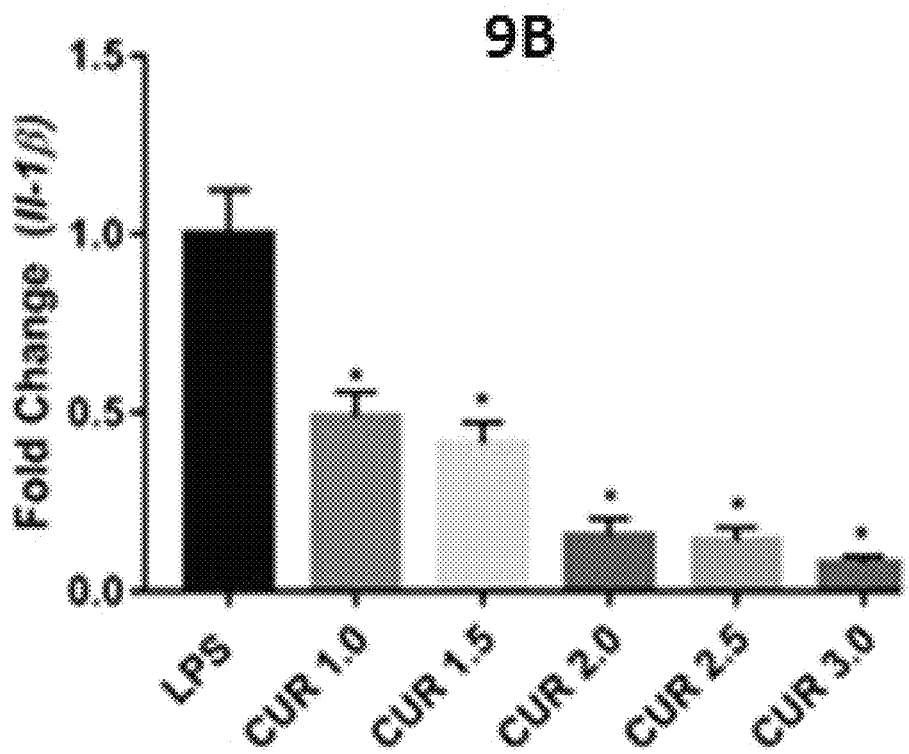
Figure 9C:
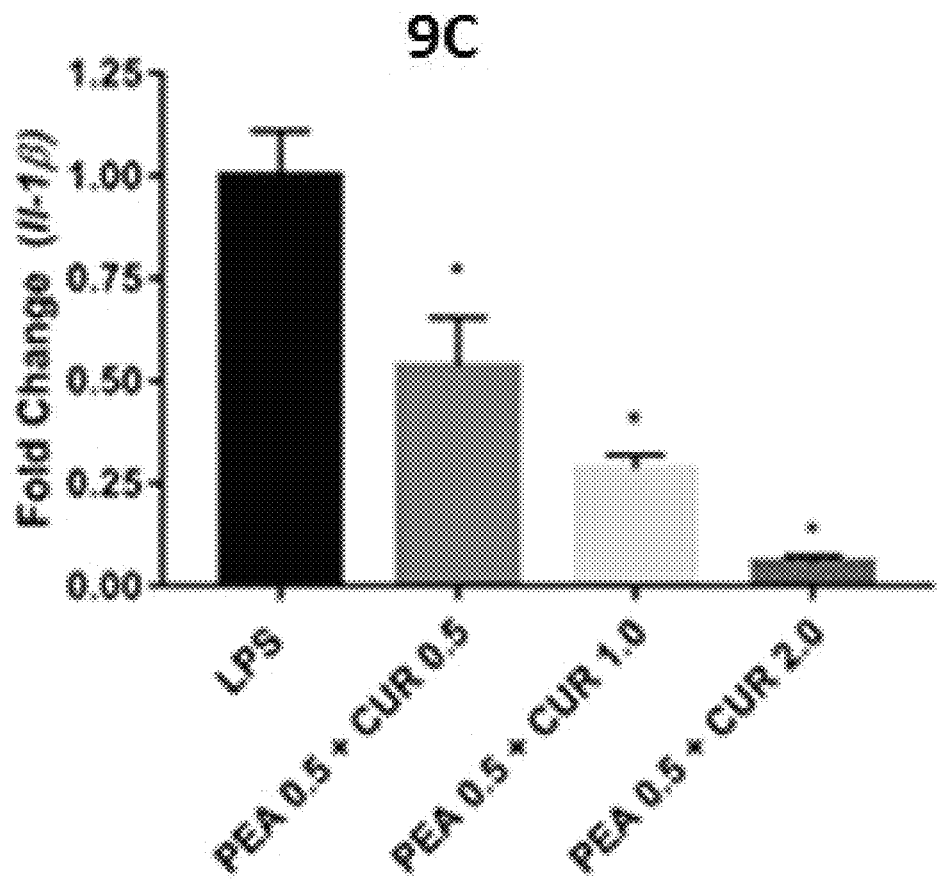
Figure 10:
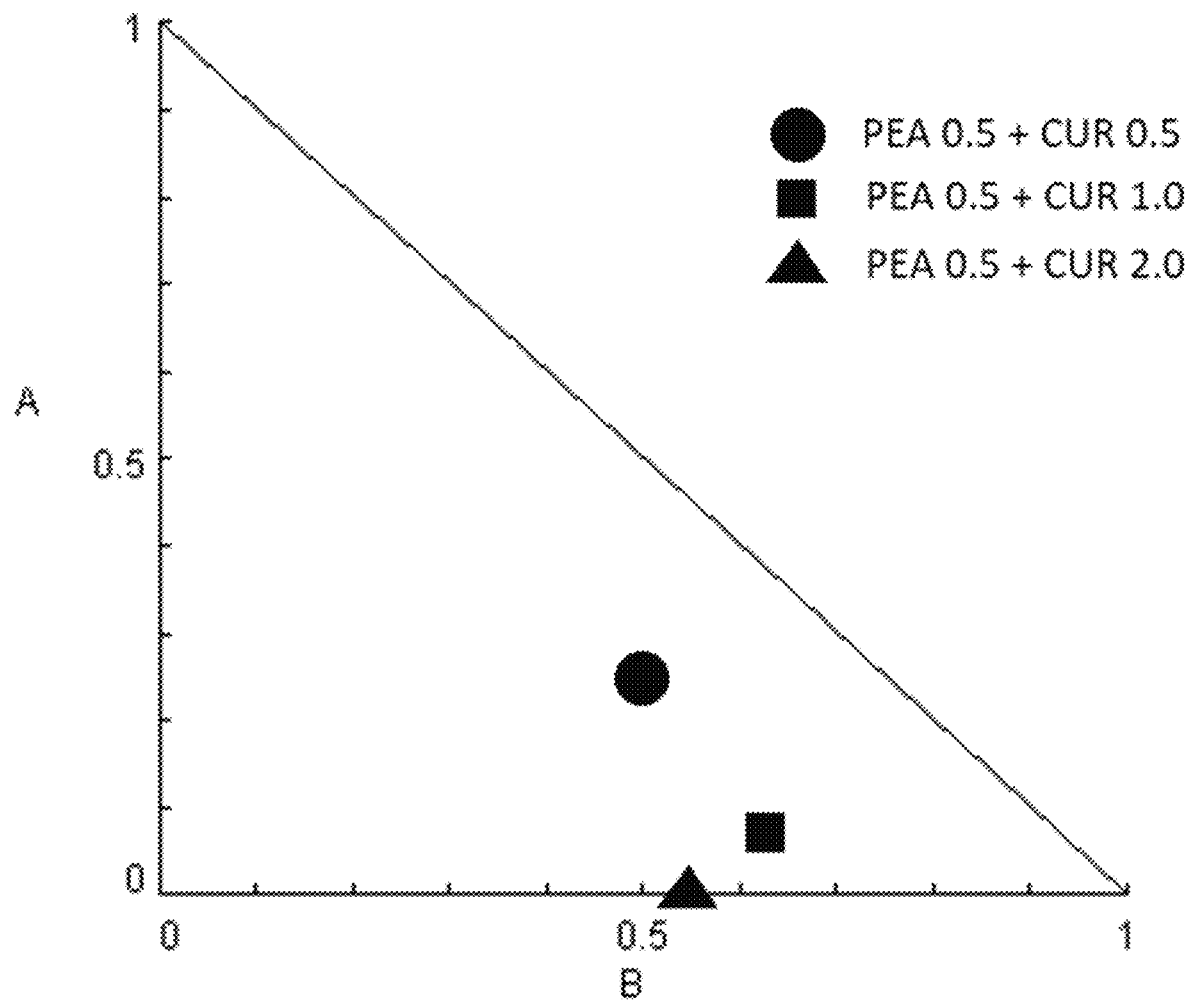
FIG. 10 shows Isobolographic analysis based on II-1β expression of murine macrophages (RAW264.4) cells treated for 9 h with PEA and curcumin alone, as well as their combinations. Isolologram was normalized to the IC50 of individual compounds.
Figure 11:
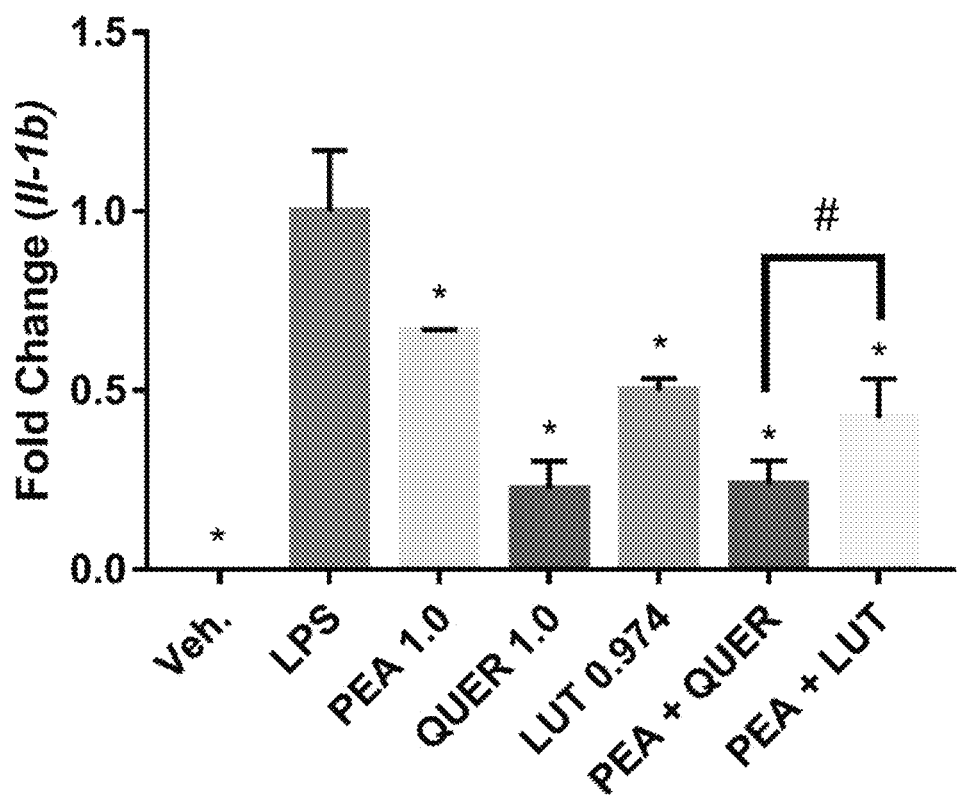
FIG. 11 is a bar graph of mRNA expression of IL-1β in LPS-activated (10 ng/mL) murine macrophages (RAW264.7) treated with PEA, quercetin and luteolin at the same molarity for 9 hours. (Veh.=0.1% DMSO; * significantly different from LPS at p<0.05; ANOVA-Dunnet's Test; # significantly different from each other at P<0.05; ANOVA-Sidak). Data are means±SD.
Figure 12A:
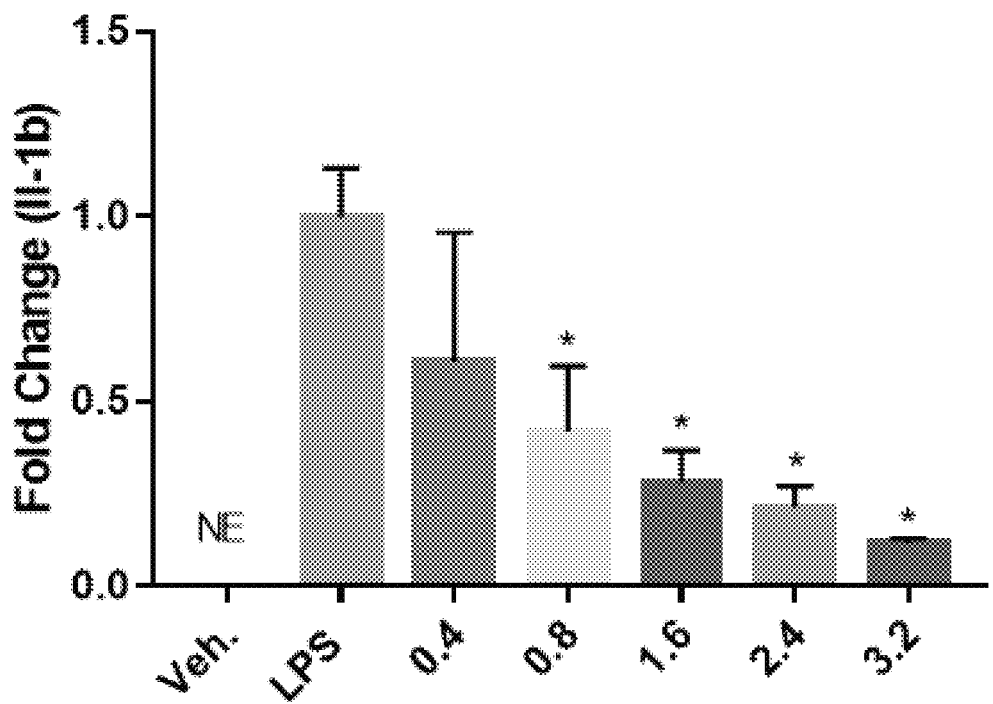
FIGS. 12A-12D show bar graphs of mRNA expression of II-1b, Cox-2, TNF-α and II-6 in LPS-activated (10 ng/mL) murine macrophages (RAW264.7) treated with increasing concentrations (mg/L) of a combined formulation containing PEA, curcuminoids extract and quercetin (5:2:1) for 9 hours. (Veh.=0.1% DMSO; NE=not expressed; * significantly different from LPS at p<0.05; ANOVA-Dunnet's Test). Data are means±SD.
Figure 12B:
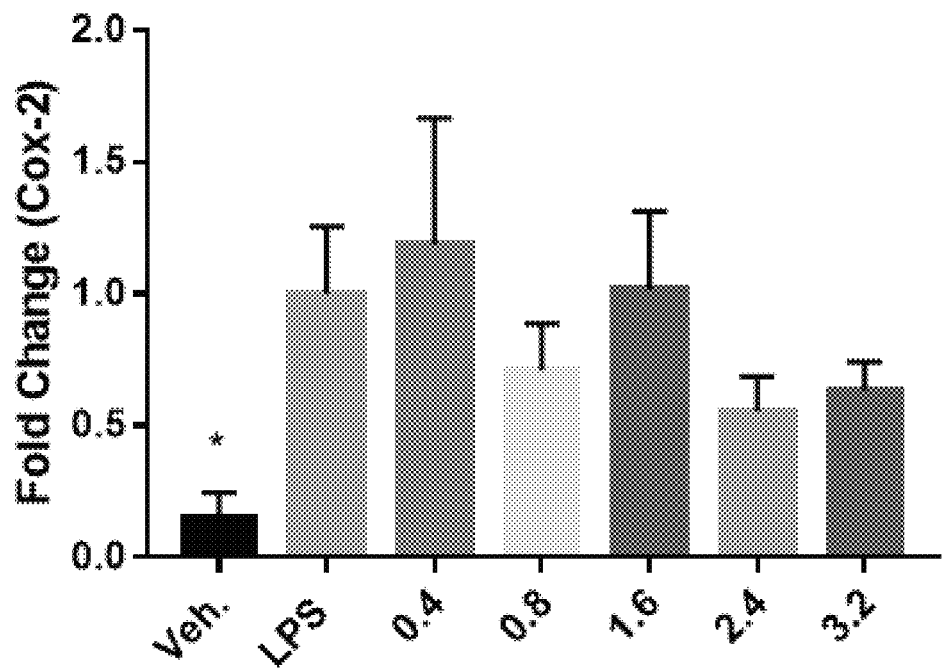
Figure 12C:
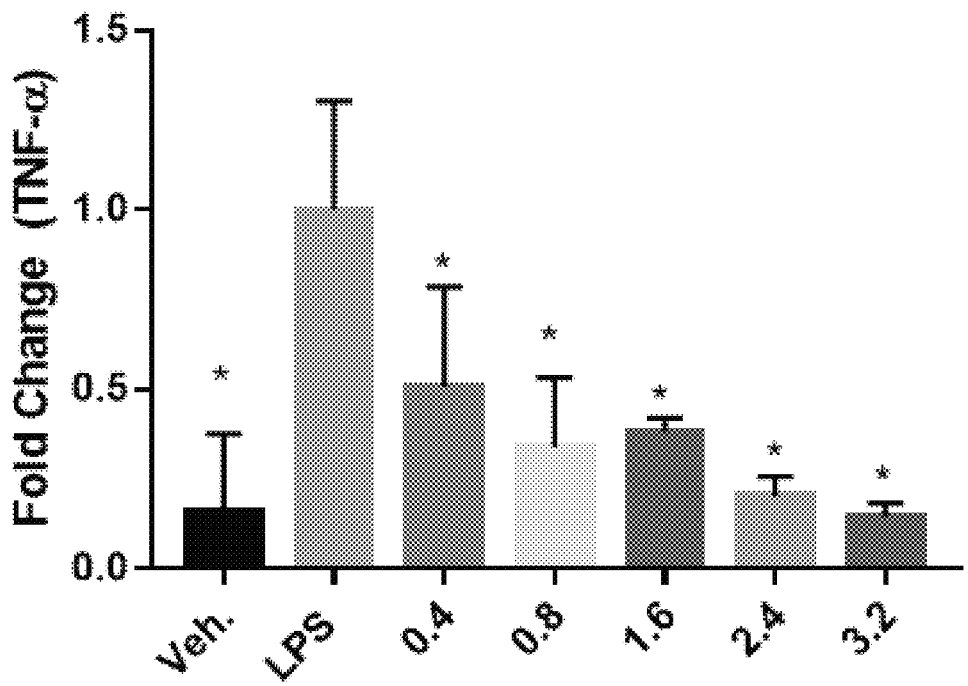
Figure 12D:
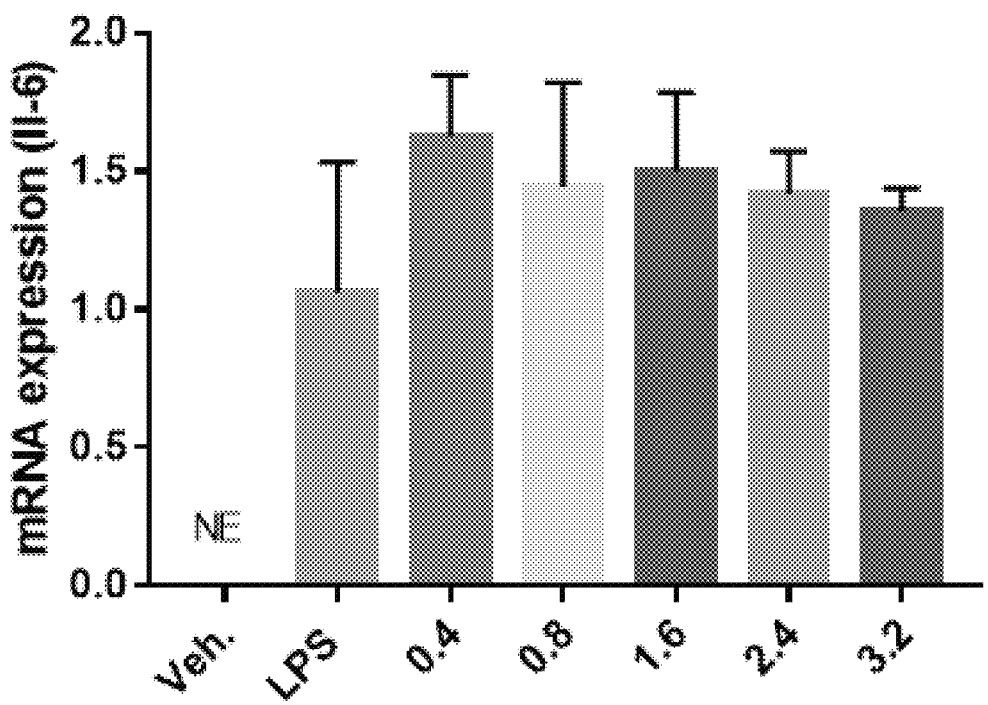

As for the treatment with curcumin, the lowest effective concentration alone was 1.0 mg/L. When in combination with PEA, concentrations as low as 0.5 mg/L of each compound (PEA 0.5+CUR 0.5) already showed significant downregulation of Il-1β, reducing mRNA expression to 54% of the LPS control (FIGS. 9A-9C). Similarly to what happened with quercetin treatments, isobolographic analysis for curcumin also showed synergistic effect for all the tested combinations (FIG. 10). Lowest CI was observed for the PEA 0.5+CUR 2.0 combination.

The Combination of PEA and Quercetin is More Effective than PEA and Luteolin

The combination of PEA and luteolin has been reported in the literature as having neuroprotective activity in response to different harmful stimuli to the central nervous system (Caltagirone et al., 2016; Crupi et al., 2016; Esposito et al., 2016; Parrella et al., 2016; Siracusa et al., 2016). We tested the combination of PEA and luteolin in our proposed model (RAW264.7 murine macrophages) to determine if the combination with this polyphenol is any better than quercetin when tested at the same molarity. The concentration used herein was selected due to previous successful experiments showing reduction of inflammatory markers using this concentration. 1.0 mg/L of PEA, 1.0 mg/L of quercetin and 0.974 mg/L of luteoline corresponds to around 3.4 µM of each compound. The analysis of IL-1β mRNA expression showed that when used alone, quercetin was able to reduce the levels by 78% while luteolin at the same molarity reduced mRNA expression by 50%. Both were significantly different from the positive control (LPS). When in combination, PEA+QUER treatment results in a significantly lower expression of IL-1β, by Sidak's post-hoc test.

Combinations of PEA with Both Curcumin and Quercetin

Based on the previously reported results with the combination of PEA+QUER and PEA+CUR, a formulation containing the three bioactive compounds was developed. PEA (98%, micronized), curcuminoids extract (95% curcuminoids) and quercetin dihydrate were combined in a ratio of 5:2:1, in the form of a loose powder, without any other excipients. This formulation was tested in vitro to access the minimal effective concentration needed to reduce the expression of selected pro-inflammatory markers. A stock solution of the combined formulation was prepared at 3200 ppm of the combined powder (this corresponds to 2000 mg/L of PEA) by diluting the combined formulation in DMSO. This concentration ensures the maximal DMSO concentrations in the treated cells will never exceed 0.1%. The treatments were prepared by dilution of the stock solution with cell culture media (DMEM), resulting in the following concentrations:

0.4 mg/L (P 0.25: C 0.2: Q 0.05)
0.8 mg/L (P 0.5: C 0.2: Q 0.1)
1.6 mg/L (P 1.0: C 0.4: Q 0.2)
2.4 mg/L (P 1.5: C 0.6: Q 0.3)
3.2 mg/L (P 2.0: C 0.8: Q 0.4)

This means that the treatment 3.2 mg/L contains 2.0 mg/L of PEA, 0.8 mg/L of curcuminoids extract and 0.4 mg/L of quercetin, based on the 5:2:1 ratio in which the product was formulated.

Minimal Effective Concentration of Combined Formulation of PEA, Quercetin and Curcuminoids The results in FIGS. 12A-12D demonstrate that the combined formulation was effective in reducing the mRNA expression of IL-1β and TNF-α in a concentration-dependent matter, starting at very low concentrations. The lowest concentration tested was able to significantly reduce 50% of TNF-α expression. For IL-1 β, which is the biomarker selected to confirm synergistic effect due to it's consistent results, the minimal effective concentration was 0.8 mg/L (of total mixed powder), which reduced 58% of the mRNA expression. This corroborates to the fact that the combined formulation is very effective even at low concentrations. Consistent with previous experiments, it was not possible to detect an effect of treatments in the expression of Cox-2.

Animal Study of Anti-Inflammatory Compositions in Canine Arthritis

The aim of this study was to assess the effectiveness and pharmacological effect of oral administration of a combined formulation of Palmitoylethanolamide (PEA) with both Curcumin and Quercetin on improvement of canine osteoarthritis (OA). Owners of dogs with arthritis were recruited through advertisements or during clinical contact. Eligible dogs weighed at least 20 kg, were between 1 and 12 years old, and presented radiographic signs of OA in the shoulder, elbow, hip joint and/or stifle. The pathology was determined to be the cause of lameness by an orthopedic examination by a veterinarian using X rays and physical/orthopedic examination. No concurrent treatment for OA was allowed during the study. Pregnant bitches, dogs with a neurological or musculoskeletal pathology other than OA, and dogs that had had orthopedic surgery within the same year were excluded.

OA affected dogs were treated with PEA+Curcumin and Quercetin formulation. Dogs were examined by physical/orthopedic exam and radiographic analysis.

Canine Brief Pain Inventory (CBPI) Questionnaire

Owners were asked to complete the CBPI questionnaire addressing the dog's OA pain and function prior to enrollment, and at the follow-up visits thereafter. The questionnaire was to be completed by the same owner at all visits, and owners were directed to base their answers on their observations of the preceding seven days.

Ground Reaction Force (GRF) Analysis

All dogs had their gait analyzed objectively by measuring ground reaction forces (GRFS) with a biomechanical force plate. (performed by veterinarian or veterinary personnel)

Synovial Fluid Collection:

For arthrocentesis, dogs were sedated with medetomidine hydrochloride (0.02 mg/kg intravenously) and synovial fluid (SF) was aspirated under aseptic conditions from the affected joints. For cytokine analysis, one aliquot of SF was centrifuged (5 min, 450 G) within 15 min and the supernatant transferred to cryotubes and immediately stored at −80° C., or placed in liquid nitrogen until transferred to −80° C. (performed by veterinarian or veterinary personnel at the small animal clinic)

Blood Collection:

Blood samples were collected for routine hematology (complete blood count tests) and biomarker analysis at study days 0 and 8. (Collection performed by veterinarian or veterinary personnel at the small animal clinic)

Biomarkers in Blood and Synovial Fluid

Samples were analyzed by Lurninex for protein quantification: IL-6, Keratan sulfate (KS), Chondroitin sulfate (CS), and stromelysin (MMP-3) and other inflammation associated biomarkers. (Biomarker analysis performed in Dr. Talcott s Lab)

Preliminary Outcomes

The study is ongoing, and it is expected this study will provide valuable information about how OA dogs respond to a combined treatment of PEA with Curcumin and Quercetin, so that we are able to safely design a complete clinical trial to further access the potential in vivo synergistic effect of that combination on canine osteoarthritis. Two dogs have completed the study, and results for these dogs demonstrated improved weight bearing in both patients with an improvement in ground reaction forces of up to about 13% over the 8 week course of the study. Some of the dogs demonstrated positive treatment effect for both pain severity and pain interference using the CBPI assessment.

CONCLUDING REMARKS

Data from this study showed that PEA alone is a potent agent against inflammation and that polyphenolic compounds can interact synergistically with PEA, showing a remarkable effect on downregulation of inflammation at the mRNA level. The combination of PEA with quercetin and curcuminoids showed remarkable potency and synergistic benefits. Although preliminary, canine studies demonstrated some improvements in both the severity of pain and weight bearing ability.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES

Crupi, R., Impellizzeri, D., Bruschetta, G., Cordaro, M., Paterniti, I., Siracusa, R., . . . Esposito, E. (2016). Co-ultramicronized palmitoylethanolamide/luteolin promotes neuronal regeneration after spinal cord injury. Frontiers in Pharmacology, 7(MAR), 1-12.

Cerrato S, Brazis P, della Valle M F, Miolo A, Puigdemont A. 2010. Effects of palmitoylethanolamide on immunologically induced histamine, PGD2 and TNFα release from canine skin mast cells. Vet. Immunol. Immunopathol. 133:9-15.

Chou T C, Talalay P. 1984. Quantitative analysis of dose-effect relationships: the combined effects of multiple drugs or enzyme inhibitors. Adv. Enzyme Regul. 22:27-55.

Chuang C, Martinez K, Xie G, Kennedy A, Bumrungpert A, Overman A, Jia W, Mcintosh M K. 2010. Quercetin is equally or more effective than resveratrol in attenuating tumor necrosis factor-a-mediated inflammation and insulin resistance in primary human adipocytes 1-3. Am. J. Clin. Nutr. 92:1511-1521.

Cordaro M, Impellizzeri D, Paterniti I, Bruschetta G, Siracusa R, De Stefano D, Cuzzocrea S, Esposito E. 2016. Neuroprotective Effects of Co-UltraPEALut on Secondary Inflammatory Process and Autophagy Involved in Traumatic Brain Injury. J. Neurotrauma 33:132-46.

Cremon C, Stanghellini V, Barbaro M R, Cogliandro R F, Bellacosa L, Santos J, Vicario M, Pigrau M. 2017. Randomised clinical trial: the analgesic properties of dietary supplementation with palmitoylethanolamide and polydatin in irritable bowel syndrome. Aliment. Pharmacol. Ther. 45:909-922.

Crupi, R., Impellizzeri, D., Bruschetta, G., Cordaro, M., Paterniti, I., Siracusa, R., . . . Esposito, E. (2016). Co-ultramicronized palmitoylethanolamide/luteolin promotes neuronal regeneration after spinal cord injury. Frontiers in Pharmacology, 7(MAR), 1-12.

Di Paola R, Fusco R, Gugliandolo E, Crupi R, Evangelista M, Granese R, Cuzzocrea S. 2016. Co-micronized palmitoylethanolamide/polydatin treatment causes endometriotic lesion regression in a rodent model of surgically induced endometriosis. Front. Pharmacol. 7:1-13.

Esposito, E., Impellizzeri, D., Bruschetta, G., Cordaro, M., Siracusa, R., Gugliandolo, E., . . . Cuzzocrea, S. (2016). A new co-micronized composite containing palmitoylethanolamide and polydatin shows superior oral efficacy compared to their association in a rat paw model of carrageenan-induced inflammation. European Journal of Pharmacology, 782, 107-118.

Guha, Mausumee, and Nigel Mackman. "LPS induction of gene expression in human monocytes." Cellular signalling 13.2 (2001): 85-94.

Karuppagounder V, Arumugam S, Thandavarayan R A, Pitchaimani V, Sreedhar R, Afrin R, Harima M, Suzuki H, Nomoto M, Miyashita S, et al. 2014. Resveratrol attenuates HMGB1 signaling and inflammation in house dust mite-induced atopic dermatitis in mice. Int. Immunopharmacol. 23:617-623.

Karuppagounder V, Arumugam S, Thandavarayan R A, Sreedhar R, Giridharan V V., Watanabe K. 2016. Molecular targets of quercetin with anti-inflammatory properties in atopic dermatitis. Drug Discov. Today 21:632-639.

Kocaadam B, Sanlier N. 2017. Curcumin, an active component of turmeric (*Curcuma longa*), and its effects on health. Crit. Rev. Food Sci. Nutr. 57:2889-2895.

Murray, P. J. and Wynn, T. A., 2011. Protective and pathogenic functions of macrophage subsets. Nat. Rev. Immunol., 11:723-737.

Parrella E, Porrini V, Iorio R, Benarese M, Lanzillotta A, Mota M, Fusco M, Tonin P, Spano P F, Pizzi M. 2016. PEA and luteolin synergistically reduce mast cell-mediated toxicity and elicit neuroprotection in cell-based models of brain ischemia. Brain Res. 1648:409-417.

Siracusa, R., Paterniti, I., Bruschetta, G., Cordaro, M., Impellizzeri, D., Crupi, R., . . . Esposito, E. (2016). The Association of Palmitoylethanolamide with Luteolin Decreases Autophagy in Spinal Cord Injury. Molecular Neurobiology, 53(6), 3783-3792.

Vaia M, Petrosino S, Filippis D De, Negro L, Guarino A, Carnuccio R, Marzo V Di, Iuvone T. 2016. Palmitoylethanolamide reduces inflammation and itch in a mouse model of contact allergic dermatitis. Eur. J. Pharmacol. 791:669-674.

The present disclosure will be better understood upon reviewing the following aspects, which should not be confused with the claims. Each of the numbered aspects below can, in some instances, be combined with other numbered aspects below and/or can be combined with any other aspects in this disclosure even if, for the sake of clarity and brevity, such aspects are not explicitly described in combination here.

Aspect 1. A pharmaceutical or nutraceutical formulation for treating inflammation in a subject in need thereof, the pharmaceutical or nutraceutical formulation comprising an effective amount of (i) palmitoylethanolamide or a derivative thereof, and (ii) one, two, three or more different small-molecule polyphenols or derivatives thereof to alleviate one or more causes or symptoms of the inflammation in the subject.

Aspect 2. The pharmaceutical or nutraceutical formulation according to any one of aspects 1-16, wherein a first ratio of (i) a mass of the palmitoylethanolamide or derivative thereof in the formulation to (ii) a mass of the one or more small-molecule polyphenols or derivatives thereof in the formulation is about 0.1 to 10, about 0.1 to 5.0, about 0.25 to about 3.0, about 0.25 to about 2.5, about 0.5, about 1.0, about 1.5, about 2.0, or about 2.5.

Aspect 3. The pharmaceutical or nutraceutical formulation according to any one of aspects 1-16, wherein the formulation comprises palmitoylethanolamide and one or both of quercetin and curcumin.

Aspect 4. The pharmaceutical or nutraceutical formulation according to any one of aspects 1-16, wherein the formulation comprises (i) palmitoylethanolamide or a derivative thereof, (ii) quercetin or a derivative thereof, and (iii) curcumin or a derivative thereof; wherein components (i)-(iii) are present at a mass ratio of about (i) 4 mg to 6 mg of palmitoylethanolamide or a derivative thereof to (ii) about 0.5 to 2.5 mg curcumin or a derivative thereof, and (iii) about 0.5 mg to 1.5 mg quercetin or a derivative thereof.

Aspect 5. The pharmaceutical or nutraceutical formulation according to any one of aspects 1-16, wherein the one or more small-molecule polyphenols are selected from the group consisting of rutin, quercetin, daidzein, daidzin, genistein, myricetin, hesperidin, neohesperidin, hesperetin, naringin, naringenin, curcumin, desmethoxycurcumin, bis-demethoxycurcumin, tetrahydrocurcumin, astragalin, kaempferol, resveratrol apigenin, delphinidin, delphin, peonidin, peonin, petunin, malvidin, cyanidin, pelargonidin, caffeic acid, chlorogenic acids, catechin, epicatechin, epigallocatechin gallate, ferulic acid, boswellic acids, rosmarinic acid, ellagic acid, p-coumaric acid, green tea polyphenols, and derivatives thereof.

Aspect 6. The pharmaceutical or nutraceutical formulation according to any one of aspects 1-16, wherein the one or more causes or symptoms of the inflammation comprise pain, swelling, stiffness, tenderness, redness, warmth, elevated inflammatory cytokines or other markers of inflammatory disease or a combination thereof.

Aspect 7. The pharmaceutical or nutraceutical formulation according to any one of aspects 1-16, wherein the formulation is a topical formulation; and wherein the topical formulation is selected from the group consisting of a cream, an ointment, a salve, a spray, a gel, a lotion, an emulsion, a liquid, and a transdermal patch.

Aspect 8. The pharmaceutical or nutraceutical formulation according to any one of aspects 1-16, wherein the topical formulation comprises one or more chemical penetration enhancers, oils, lipids, membrane permeability agents, membrane transport agents, emollients, surfactants, stabilizers, or a combination thereof.

Aspect 9. The pharmaceutical or nutraceutical formulation according to any one of aspects 1-16, wherein the formulation is an enteral formulation; and wherein the enteral formulation is selected from the group consisting of tablets, capsules, solutions, suspensions, syrups, lozenges, and dry powders.

Aspect 10. The pharmaceutical or nutraceutical formulation according to any one of aspects 1-16, wherein the enteral formulation further comprises one or more diluents, preservatives, binders, lubricants, disintegrators, swelling agents, fillers, stabilizers, or a combination thereof.

Aspect 11. The pharmaceutical or nutraceutical formulation according to any one of aspects 1-16, wherein the subject is a human.

Aspect 12. The pharmaceutical or nutraceutical formulation according to any one of aspects 1-16, wherein the subject is a mammal.

Aspect 13. The pharmaceutical or nutraceutical formulation according to any one of aspects 1-16, wherein the subject is a veterinary animal such as a dog, a cat, or a horse.

Aspect 14. The pharmaceutical or nutraceutical formulation according to any one of aspects 1-16, wherein the therapeutically effective amount is less than a therapeutically effective amount of the otherwise same formulation except without the one or more small-molecule polyphenols or derivatives thereof.

Aspect 15. The pharmaceutical or nutraceutical formulation according to any one of aspects 1-16, wherein the effective amount is less than 80% of a effective amount of the otherwise same formulation except without the one or more small-molecule polyphenols or derivatives thereof.

Aspect 16. The pharmaceutical or nutraceutical formulation according to any one of aspects 1-16, further comprising a pharmaceutically acceptable carrier.

Aspect 17. A method of treating or alleviating one or more causes or symptoms of inflammation in a subject in need thereof, the method comprising administering a therapeutically effective amount of a pharmaceutical formulation according to any one of aspects 1-16.

Aspect 18. A method of treating or alleviating one or more causes or symptoms of inflammation in a subject in need thereof, the method comprising administering an effective amount of (i) palmitoylethanolamide or a derivative thereof and (ii) one or more small-molecule polyphenols or derivatives thereof to alleviate the one or more causes or systems of inflammation in the subject.

Aspect 19. The method according to any one of aspects 17-27, wherein the administration comprises administering palmitoylethanolamide and one or both of quercetin and curcumin.

Aspect 20. The method according to any one of aspects 17-27, wherein the one or more small-molecule polyphenols are selected from the group consisting of rutin, quercetin, daidzein, daidzin, genistein, myricetin, hesperidin, neohesperidin, hesperetin, naringin, naringenin, curcumin, desmethoxycurcumin, bis-demethoxycurcumin, tetrahydrocurcumin, turmerones, astragalin, kaempferol, resveratrol apigenin, delphinidin, delphin, peonidin, peonin, petunin, malvidin, cyanidin, pelargonidin, caffeic acid, chlorogenic acids, catechin, epicatechin, epigallocatechin gallate, ferulic acid, benzoic acid, benzaldehydes, boswellic acids, capsaicin, capsaicinoids, rosmarinic acid, ellagic acid, resveratrol, pterostilbene or p-coumaric acid. The small molecule polyphenol may be in aglycone or glucoside form, or as a monomer, oligomer or polymer.

Aspect 21. The method according to any one of aspects 17-27, wherein the one or more causes or systems of the inflammation comprise pain, swelling, stiffness, tenderness, redness, warmth, elevated inflammatory markers, or a combination thereof.

Aspect 22. The method according to any one of aspects 17-27, wherein the administration comprises topical administration.

Aspect 23. The method according to any one of aspects 17-27, wherein the administration comprises enteral administration.

Aspect 24. The method according to claim 17 or claim 18, wherein the effective amount is less than an effective amount of the otherwise same method or the otherwise same formulation except without administering the one or more small-molecule polyphenols or derivatives thereof.

Aspect 25. The method according to any one of aspects 17-27, wherein the effective amount is less than 90%, less than 80%, less than 70%, or less than 60% of an effective amount of the otherwise same method or the otherwise same formulation except without administering the one or more small-molecule polyphenols or derivatives thereof.

Aspect 26. The method according to any one of aspects 17-27, wherein the effective amount is about 1 mg or about 2.5 mg of active agents and up to about 25 mg or 50 mg of active agents per pound of body weight.

Aspect 27. The method according to any one of aspects 17-27, wherein the method comprises: (i) administering one or more loading dosages of about 5 mg or about 7.5 mg of active agents and up to about 15 mg, 20 mg, or 25 mg of active agents per pound of body weight; and (ii) administering one or more maintenance dosages of about 2.5 mg to about 7.5 mg of active agents per pound of body weight.

We claim:

1. A formulation comprising an effective amount of (i) palmitoylethanolamide (ii) quercetin or a dihydrate thereof, and (iii) curcumin,
wherein components (i)-(iii) are present at a mass ratio of (i) 4 to 6 of palmitoylethanolamide (ii) 0.5 to 2.5 curcumin, and (iii) 0.5 to 1.5 quercetin or the dihydrate thereof, and
wherein the mass ratio of the curcumin to quercetin or the dihydrate thereof is from 1:1 to 3:1.

2. The formulation according to claim 1, wherein the formulation further comprises a compound selected from the group consisting of rutin, daidzein, daidzin, genistein, myricetin, hesperidin, neohesperidin, hesperetin, naringin, naringenin, desmethoxycurcumin, bis-demethoxycurcumin, tetrahydrocurcumin, astragalin, kaempferol, resveratrol apigenin, delphinidin, delphin, peonidin, peonin, petunin, malvidin, cyanidin, pelargonidin, caffeic acid, chlorogenic acids, catechin, epicatechin, epigallocatechin gallate, ferulic acid, boswellic acids, rosmarinic acid, ellagic acid, and p-coumaric acid.

3. The formulation according to claim 1, wherein the formulation is a topical formulation; and
wherein the topical formulation is selected from the group consisting of a cream, an ointment, a salve, a spray, a gel, a lotion, an emulsion, a liquid, and a transdermal patch.

4. The formulation according to claim 1, wherein the formulation is an enteral formulation; and
wherein the enteral formulation is selected from the group consisting of tablets, capsules, solutions, suspensions, syrups, lozenges, and dry powders.

5. The formulation according to claim 1, wherein the subject is a veterinary animal.

6. The formulation according to claim 1, wherein the effective amount is less than 80% of an effective amount of the otherwise same formulation except without curcumin and quercetin or the dihydrate thereof.

7. The formulation according to claim 1, wherein palmitoylethanolamide is micronized.

8. The formulation according to claim 1, wherein a first ratio of (i) a mass of palmitoylethanolamide in the formulation to (ii) a mass of quercetin or the dihydrate thereof in the formulation is about 1:1 to about 6:1.

9. The formulation according to claim 1, wherein a first ratio of (i) a mass of palmitoylethanolamide in the formulation to (ii) a mass of curcumin in the formulation is about 1:1 to about 6:1.

10. The formulation according to claim 1, wherein the formulation has a first ratio of (i) a mass of palmitoylethanolamide in the formulation to (ii) a mass of curcumin in the formulation is about 5:3 to about 5:1 and a second ratio of (i) a mass of palmitoylethanolamide in the formulation to (ii) a mass of quercetin or the dihydrate thereof in the formulation is about 6:1 to about 5:2.

* * * * *